US009682042B2

(12) United States Patent
Cardona Iglesias et al.

(10) Patent No.: US 9,682,042 B2
(45) Date of Patent: Jun. 20, 2017

(54) MTB-C VACCINE AGAINST ASTHMA

(75) Inventors: Pere Joan Cardona Iglesias, Barcelona (ES); Isabel Amat Riera, Barcelona (ES); Blanca Reyes Moreno, Barcelona (ES); Maria Mercè Amat Fabregat, Barcelona (ES)

(73) Assignee: ARCHIVEL FARMA, S.L., Badalona (ES)

( * ) Notice: Subject to any disclaimer, the term of this patent is extended or adjusted under 35 U.S.C. 154(b) by 0 days.

(21) Appl. No.: 14/371,613

(22) PCT Filed: Jan. 12, 2012

(86) PCT No.: PCT/IB2012/000353
§ 371 (c)(1),
(2), (4) Date: Jan. 23, 2015

(87) PCT Pub. No.: WO2013/104943
PCT Pub. Date: Jul. 18, 2013

(65) Prior Publication Data
US 2015/0132364 A1 May 14, 2015

(51) Int. Cl.
*A61K 51/00* (2006.01)
*A61K 39/00* (2006.01)
*A61K 39/04* (2006.01)
*A61K 9/127* (2006.01)
*A61K 45/06* (2006.01)

(52) U.S. Cl.
CPC ............ *A61K 9/127* (2013.01); *A61K 39/001* (2013.01); *A61K 39/04* (2013.01); *A61K 45/06* (2013.01); *A61K 2039/55555* (2013.01); *A61K 2039/577* (2013.01)

(58) Field of Classification Search
CPC ........ A61K 39/00; A61K 39/02; A61K 39/04; A61K 39/35
See application file for complete search history.

(56) References Cited

U.S. PATENT DOCUMENTS

| | | | |
|---|---|---|---|
| 2003/0022854 A1 | 1/2003 | Dow et al. |
| 2007/0059318 A1 | 3/2007 | Balu-Iyer et al. |
| 2009/0081284 A1 | 3/2009 | Kojima et al. |

FOREIGN PATENT DOCUMENTS

| | | | |
|---|---|---|---|
| CA | 2453959 | A1 | 1/2003 |
| CA | 2666322 | A1 | 10/2008 |
| CN | 1874785 | A | 12/2006 |
| EP | 1690549 | A1 | 8/2005 |
| EP | 2090318 | A1 | 8/2009 |
| EP | 2332571 | A1 | 6/2011 |
| ES | 2231037 | A1 | 5/2005 |
| WO | WO-96/26288 | A1 | 8/1996 |
| WO | WO-99/65465 | A1 | 12/1999 |
| WO | WO-2006/088492 | A1 | 8/2006 |
| WO | WO-2006/117240 | A2 | 11/2006 |
| WO | WO-2007/109221 | A1 | 9/2007 |
| WO | WO-2008/051245 | A1 | 5/2008 |
| WO | WO-2009/089535 | A2 | 7/2009 |
| WO | WO-2010/121618 | A1 | 10/2010 |
| WO | WO-2012/080369 | A1 | 6/2012 |

OTHER PUBLICATIONS

Cardona, PJ. et al., "Immunotherapy with fragmented *Mycobacterium tuberculosis* cells increases the effectiveness of chemotherapy againsts a chronical infection in a murine model of tuberculosis", *Vaccine*, Elsevier Ltd., GB, vol. 23, No. 11, Feb. 3, 2005, pp. 1393-1398.

Crowe, J.H, et al. "Interactions of Sugars with Membranes", *Biochimica et Biophysica Acta*, Elsevier, NL, vol. 947, No. 2, Jun. 9, 1988, pp. 367-384.

Deng Y, et al., "The antiasthma effect of neonatal BCG vaccination does not depend on the Th17/Th1 bul IL-17/IFN-γbalance in a BALB/c mouse asthma model", *J. Clin. Immunol.* Jun. 2011: 31(3):419-29.

Extended European Search Report for EP 11150072, dated May 31, 2011.

International Search Report & Written Opinion issued in PCT/IB2012/000353, date of mailing Aug. 14, 2012.

International Search Report for PCT/EP2012/050080, mailed Mar. 2, 2013.

Mir F, et al., "A Multicistronic DNA Vaccine Induces Significant Protection against Tuberculosis in Mice and Offers Flexibility in the Expressed Antigen Repertoire", *Clinical and Vaccine Immunology*, 2009, 16(10):1467-1475.

Mohammed, AR, et al., "Increased potential of a cationic liposome-based delivery system; Enhancing stability and sustained immunological activity in pre-clinical development", *European Journal of Pharmaceutics and Biopharmaceutics*, Elsevier Science Publishers B.V., Amsterdam, NL, vol. 76, No. 3, Nov. 1, 2010, pp. 404-412.

Mohammed, AR, et al., "Lyophilisation and sterilisation of liposomal vaccines to produce stable and sterile products", *Methods: A Companion to Methods in Enzymology*, Academic Press Inc., New York, NY, US, vol. 40, No. 1, Sep. 1, 2006, pp. 30-38.

(Continued)

*Primary Examiner* — Rodney P Swartz
(74) *Attorney, Agent, or Firm* — McCarter & English, LLP; Danielle L. Herritt; Jill Ann Mello

(57) ABSTRACT

The invention relates to an agent for the treatment or prevention of an allergic condition, such as asthma, in a mammal. The agent comprises fragments of a *Mycobacterium tuberculosis*-complex (MTB-C) strain. These particular fragments may be from a virulent MTB-C strain and/or in the form of a liposome composition. The agent may include further components, such as a liposome-forming agent and/or particular proteins from the MTB-C strain.

A particular allergic response that may be treated by the agent of the invention is allergic asthma. A pharmaceutical composition comprising the agent is also provided.

Administration of the agent described herein significantly attenuates airway hyperresponsiveness, eosinophilia and lymphocytosis in the airways of sensitized animals. The effectiveness of the agent exceeds on all the evaluated parameters the commercial vaccine BCG Danish 1331 Strain.

21 Claims, 14 Drawing Sheets

(56) References Cited

OTHER PUBLICATIONS

Obihara CC, et al., "*Mycobacterium tuberculosis* infection may protect against allergy in a tuberculosis endemic area", Clin. Exp. Allergy, Jan. 2006;36(1):70-6.
Orme, et al., "Preclinical testing of new vaccines for tuberculosis; A comprehensive review", *Vaccine*, Elsevier Ltd., GB, vol. 24, No. 1, Jan. 9, 2006, pp. 2-19.
Riffo-Vasquez Y, et al., "Effect of *Mycobacterium tuberculosis* chaperonins on bronchial eosinophilia and hyper-responsiveness in a murine model of allergic inflammation", *Clin. Exp. Allergy*, May 2004;34(5):712-9.
Rosenbrands, I, et al., "Cationic liposome containing mycobacterial lipids: a new powerful Th1 adjuvant system", *Infection and Immunity, American Society for Microbiology*, Washington, US, vol. 73, No. 9, Sep. 1, 2005, pp. 5817-5826.
Strauss, G et al., "Stabilization of lipid bilayer vesicles by sucrose during freezing", *Proc. Natl. Acad. USA*, Apr. 1986, vol. 83, pp. 2422-2426.
Szoka, Jr. F, et al., "Procedure for preparation of liposomes with large internal aqueous space and high capture by reverse-phase evaporation", Proc. Natl. Acad. Sci. USA, 1978, 75(9):4194-4198.
Weinrich Olsen, A, et al., "Protection of mice with tuberculosis subunit vaccine based on a fusion protein of antigen 85B and ESAT-6", *Infection and Immunity, American Society for Microbiology*, Washington, US, vol. 69, No. 5, May 1, 2001, pp. 2773-2778.
Zadi, B., et al., "A Novel Method for High-Yield Entrapment of Solutes into Small Liposomes", *Journal of Liposome Research*, Taylor & Francis, Philadelphia, PA, US, vol. 10, No. 1, Feb. 1, 2000, pp. 73-80.
Zhang GS, et al., "New insights into the effects of *Mycobacterium bovis* Bacillus Calmette-Guerin on asthma", *Chin Med. J* (Engl). Mar. 5, 2009;122(5):577-83.
Zumbuehl, O, et al., "Liposomes of controllable size in the range of 40 to 180 nm by defined dialysis of lipid/detergent mixed micelles", *Biochimica et Biophysica Acta. Biomembranes*, Amsterdam, NL., vol. 640, No. 1, Jan. 8, 1981, pp. 252-262.
Lemmer, Y. et al., "Detection of Antimycolic Acid Antiboidies by Liposomal Biosensors," *Methods in Enzymology* (2009), 464: 79-104 (2009).
Arnoldussen, D.L, et al., "BCG vaccination and allergy: A systematic review and meta-analysis", *J. Allergy Clin. Immunol.*, vol. 127, No. 1, 246-253, 2011.
Jentoft, H.F. et al., "Absence of relationship between tuberculin reactivity and asthmatic symptoms, level of $FEV_1$ and bronchial hyperresponsiveness in BCG vaccinated young adults," *Allergy*, vol. 57, pp. 336-340, 2002.
Youmans, A.S. et al., "Effect of mitochondrial stabilizers on the immunogenicity of the particulate fraction isolated from *Mycobacterium tuberculosis", Journal of Bacteriology*, vol. 97, No. 6, pp. 1346-1354, 1964.
Yadava, P., et al., "Effect of Lyophilization and Freeze-thawing on the Stability of siRNA-Liposome Complexes", AAPS PharmSciTech, vol. 9, No. 2, Jun. 2008, pp. 335-341.

1 2 3 4 5 6 7

1 2 3 4 5 6 7

MTB-C VACCINE AGAINST ASTHMA

RELATED APPLICATION

This application is a 35 U.S.C. §371 national stage filing of International Application No. PCT/IB2012/000353, filed on Jan. 12, 2012, the entire contents of which are incorporated herein by reference.

INTRODUCTION

The present invention relates to an agent for the treatment or prevention of an allergic condition, such as asthma, in a mammal, such as a human. The agent comprises fragments of a *Mycobacterium tuberculosis*-complex (MTB-C) strain.

Many substances can, in general, trigger an allergic reaction, including but not limited to, environmental factors such as pollen, dust, mold, plants like grass or trees, animal dander, food, medications or chemicals. Symptoms of allergic responses include without limitation thereto the following: itchiness, swelling, running nose, watery eyes, coughing, wheezing, trouble breathing, hives, rashes, mucus production, or, as a more severe reaction, even anaphylaxis. Allergic responses and their severity vary greatly between individuals of any given species.

It is widely recognized that the molecular basis of allergic reactions is in the mammalian immune system, which is designed to protect the body from potential harm. In individuals who show allergic reactions, the immune system reacts to allergens, i.e. substances that trigger an immune response. Typical allergens include such as pollen, mites, or molds, and these allergens are often inhalable, which makes them important triggers of allergic responses in the respiratory tract. Allergic responses are thus hypersensitive immune reactions to a substance that is harmless in healthy (non-affected) individuals, but may cause harmful symptoms in affected individuals.

A localized hypersensitivity to an allergen is also termed atopy. Atopy may have a hereditary component, although contact with the allergen must occur before the hypersensitivity reaction can develop. One of the most common allergic diseases of the respiratory tract is allergic asthma, which ranges among the most common allergic responses. In return, it is understood that allergic asthma is the most common type of asthma. About 90% of children with childhood asthma have (other) allergies, compared with about 50% of adults. Inhaling specific allergens can trigger occurrence of asthma symptoms associated with allergic asthma. Nearly every individual with asthma (allergic or nonallergic) gets worse after exercising in cold air or after inhaling any type of smoke, dust, fumes, and sometimes strong smells.

Asthma is an obstructive lung disease and one of the most common disorders encountered in clinical medicine. Asthma is typically characterized by a variable degree of airflow obstruction, airway inflammation and bronchial hyper-responsiveness. Some asthma patients also show a hypersensititvity to commonly inhaled agents, such as pollen. Asthma is a chronic inflammatory disorder of the respiratory system, leading to disruption of airway epithelium, infiltration of inflammatory cells, as well as tensions of smooth muscle. Asthma is a chronic inflammatory disorder to the respiratory system that is characterized by reversible obstruction of the airways and by tracheal and bronchial hyper-reactivity, leading to airway narrowing. It is characterized clinically by wheezing, dyspnea and cough. Although the most common form of asthma is allergic asthma, other factors contributing to asthma include infection, exercise, air pollution and possibly emotional factors. In subject suffering from asthma, the airway passages from the lungs to the nose and mouth narrow, which lead to difficulty in breathing. These symptoms occur chronically or acute, or as acute outbreaks of a chronic disease; they often times occur in response to changes in the environment, such as weather changes, presence of allergens, and/or infections of the respiratory tract. Asthma is also defined as paroxysmal or chronic dyspnoea due to lung disorder.

Without wishing to be bound to any particular theory, a genetic predisposition has often been implicated in asthma and other allergic responses. While some patients do show a family history for asthma or other allergic responses, large numbers of patients do not have a personal or family history.

Bronchial asthma is characterized by recurrent smooth muscle contraction and occurs as chronic or episodic condition or as episodically occurring symptoms of a chronic disease. It is clinically characterized by episodic or chronic wheezing, cough and feeling of tightness in the chest, limitation of air flow on lung function testing, and complete or partial reversibility of the obstructive dysfunction after a bronchodilator therapy.

The underlying syndrome of asthma is a chronic inflammation, and the lungs of patients often show hyper-inflammation. The hallmark of asthma is bronchial hyperreactivity (bronchial hyper-responsiveness). Bronchial hyperresponsiveness (or other combinations with airway or hyperreactivity) is a state characterised by easily triggered bronchospasm (contraction of the bronchioles or small airways). The principal symptom manifested by patients with asthma is airway hyperresponsiveness (AHR); i.e., excessive contractile response of the bronchial muscles in reaction to a nonspecific bronchoconstrictor such as methacholine. Methacholine (Provocholine) is a synthetic choline ester acting as a non-selective muscarinic receptor agonist in the parasympathetic nervous system. It can be used to diagnose bronchial hyperreactivity/hypersensitiveness/hyperresponsiveness (these three terms are used interchangeably) by a bronchial challenge test. To that end, chemicals like methacholine or histamine trigger bronchospasm in normal individuals as well, but individuals with bronchial hyperresponsiveness have a lower threshold.

The prevalence and severity of asthma and other atopic/allergic reactions have significantly increased since the mid of the twentieth century. Several studies have pointed at a correlation between the prevalence of atopic disorders including asthma with early life exposure to antigens. Children who are raised on farms, who have a larger number of older siblings and who attend group day care at early age seem to be largely protected against asthma and other atopic conditions. This has lead to the formulation of the "hygiene hypothesis", according to which the risk of an atiopic disease is linked to reduced microbial exposure during childhood (Strachan, B M J., 1989, 299:1259-1260; and Rook et al., Springer Semin. Immunopathol., 2004. 25: 237-255). It is currently understood that the activation of the innate immune system by antigens in exposed individuals (children) may be the molecular reason for this phenomenon. The innate immune system is based on recognition of "alien" patterns (pathogen/microbe associated patterns (PAMPs/MAMPs) and provides rapid but nonspecific response to potential pathogens (no prior exposure to a particular pathogen is required).

It is known that T-helper 2 (Th2) cytokines play an important role in allergic asthma and other allergic/atopic responses. These Th2 cytokines, including IL-4, IL-5 and IL-13 among others, induce many of the manifestations of atopy and inflammation, such as B-cell isotype switching to IgE production, eosinophil chemotaxis and activation, and also airway-specific responses such as bronchial hyperreactivity (Kline, Proc. Am. Thor. Soc., 4 (3):283-8, 2007). Eosinophil granulocytes, usually called eosinophils or eosinophiles (or acidophils), are white blood cells that are one of the immune system components responsible for combating multicellular parasites and certain infections in vertebrates. Along with mast cells, they also control mechanisms associated with allergy and asthma. They are granulocytes that develop during haematopoiesis in the bone marrow before migrating into blood. In allergic asthma, eosinophils are typically found in areas surrounding the bronchae; they are then referred to as peribronchial eosinophiles.

Since Th1 responses and Th2 responses are counter-regulatory, it was proposed that an induction of a Th1 response may protect against unwanted Th2 responses (such as in atopic conditions like allergic asthma), and that such induction of Th1 response may provide increased susceptibility to atopic asthma. However, reduced allergic disorders in children with helminthic infestations (with intense Th2 inflammation) as well as the increasing prevalence of Th1-dependent disorders (such as type 1 diabetes, inflammatory bowel disease, and multiple sclerosis) that has paralleled the asthma epidemic, suggest that the induction of Th1-driven immunity does not adequately explain the protection described by the hygiene hypothesis. Recent work has focused on the promotion of regulatory-type responses (Tregs cells), known to suppress both Th1-type and Th2-type inflammation, by pathogen-associated molecular patters (Kline et al., J allergy Clin Immunol 2005; 116:1202-5).

Allergic asthma is a disease of the airways increasingly prevalent today, the treatment of which is focused, not always successfully, towards managing symptoms.

Such treatments may involve inhalation of cortical steroids, or administration of beta agonist, methyl xanthine, cholinergic agents or leukotriene agonists. These agents however do not typically only target asthma but come with considerable side effects. The use of condition-tailored agents is therefore desired and in this sense a productive area of current research is investigating the utility of microbial products for modulation of inflammation in asthma and atopic disorders. To that end, the following agents, that have been tested in clinical trials, are used in the state of the art: (1) nucleic acids with CpG motives; (2) BCG (Bacille-Calmette Guerin, *M. bovis*) which is a living prophylactic tuberculosis vaccine and is derived from a attenuated strain of *M. bovis*; (3) an agent comprising heat-killed *Mycobacterium vaccae* (*M. vaccae*) is currently in clinical development.

1. CpG Dinucliotides:

Bacterial DNA differs from mammalian DNA in the presence of unmethylated sequence patterns of cytosine-guanine (CpG) dinucleotides, and many of the effects of bacterial DNA can be recapitulated by oligodeoxynucleotides (ODNs) containing these CpGs in specific base sequence motives (CpGoDNS). It is a hypothesis that CpG ODNS prevent a topic asthma by causing a regulation in the Th1/Th2 balance. The role of CpGDNA as possible immunomodulator in asthma patient is reviewed for example by Kline et al., J allergy Clin Immunol 2005; 116:1202-5.

2. BCG Tuberculosis Vaccine:

As some studies have proposed that a decline in bacterial infections such as tuberculosis is a factor underlying the rising prevalence and severity of atopic disorder in developed countries, BCG (*Bacillus* Calmette-Guerin) prophylactic vaccine against *Mycobacterium tuberculosis* (*M. tuberculosis*), that consists on a live strains of *Mycobacterium bovis* attenuated has been tested in preventive therapy of asthma. There are however still conflicting ideas about the inverse relationship between BCG vaccination and asthma since different epidemiological studies have shown opposite results. The biological explanation for the BCG as an agent that inhibits allergic responses is generally based on its capability to stimulate the production of Th1 cytokines. The role of BCG in asthma has been reviewed by Zhang et al., Chin. Med. J., 2009, 122(5):577-583.

3. *Mycobacterium* Vaccae:

A third approach, is based on the hypothesis that the vaccine *Mycobacterium vaccae* (*M. vaccae*), initially in development to Tuberculosis treatment, can attenuate asthmatic reactions that occur following allergen challenge. *Mycobacterium vaccae* vaccine consists of heat-killed strain of *M. vaccae*. It was suggested that heat killed *Mycobacterium vaccae* may be able to modulate the Th1/Th2 balance. The role of *Mycobacterium vaccae* has been tested in some clinical trials with positive results (Camporota et al., Eur. Respir. J., 2003, 21: 287-293).

In view of the shortcomings of each of the approaches (1) to (3) above, it is necessary to develop new compounds and compositions likely to improve the general condition and which can be used as preventive and/or therapeutic agent.

PROBLEM TO BE SOLVED

The goal of the present invention is the provision of an improved agent for the therapy and prophylaxis of allergic conditions including asthma and rhinitis in humans and other mammals.

BRIEF DESCRIPTION OF THE INVENTION

The present invention relates to an agent comprising fragments of a *Mycobacterium tuberculosis*-complex (MTB-C) strain for use in prevention or therapy of an allergic response of a human or animal. In particular embodiments, the agent is further characterized by at least one of the following characteristics:

1. The fragments originate from a virulent *Mycobacterium tuberculosis*-complex (MTB-C);
2. the agent is obtainable by cultivating the MTB-C strain and, subsequently, homogenising the cell culture in the presence of a preferably non-ionic surfactant;
3. the agent is a liposome formulation comprising a liposome forming agent and sucrose;
4. the agent is a liposome formulation comprising a liposome forming agent and having a z-average size of the particles of 150 nm or less.

While each of the features 1 to 4 above may be fulfilled alone, any one or more of them may also be fulfilled in combination. Thus, for example, also in the case of the characteristics 1 and 2, the agent may be in the form of a liposome formulation, and also in the case of the characteristics 1 to 3 the z-average size of the liposome particles may be 150 nm or less. In a particular embodiment, the z-average size of the liposome particles may be in the range from 40 to 135 nm, more preferably from 55 to 125 nm, while, alternatively, the liposome formulation of the invention may be an emulsion, such that the z-average size of the particles may be below 40 nm. It is preferred that the particle size is distributed evenly, so that the polydispersity index of the particles is 0.4 or less, preferably 0.3 or less.

Also the particles according to any of the characteristics 2 to 4 above may be further characterized in that the *Mycobacterium tuberculosis*-complex (MTB-C) strain is a virulent *Mycobacterium tuberculosis*-complex (MTB-C) strain. In a particular embodiment of the invention, the *Mycobacterium tuberculosis*-complex (MTB-C) strain is the MTB-C strain NCTC 13536, deposited in 2010 at the NCTC in London.

The agent of the invention, which may be a liposome formulation, can additionally comprise a tensioactive agent (d). The agent of the invention may also additionally comprise one or more non-ionic surfactants (e). The non-ionic surfactant is preferably selected from the group consisting of alkylphenol ethoxylates, sorbitan ester ethoxylates, and more preferably a octylphenol ethoxylate.

The fragments of MTB-C of the agent of the invention may also be or comprise cell wall fragments.

The agent of the invention may further be characterized by one or more of the following: (i) The liposome forming agent may be a hydrogenated, partially hydrogenated or non-hydrogenated phospholipid, preferably lecithin, and most preferably soy lecithin. (ii) The tensioactive agent is selected from cholate, deoxycholate, cholesterol and cholesterol hemisuccinate. (iii) The fragments are or comprise protein fragments of MTB-C. In a particular embodiment thereof the agent may comprise at least two, preferably three, more preferably four, and most preferably all of the following:

(i) a first polypeptide having a molecular weight of about 70 kDa, having a mass fingerprint similar to a mass fingerprint of *M. tuberculosis* HSP70 protein (Rv0350),
(ii) a second polypeptide having a molecular weight of about 38 kDa, having a mass fingerprint similar to a mass fingerprint of *M. tuberculosis* 38 kDa protein (Rv0934),
(iii) a third polypeptide having a molecular weight of about 30 kDa, having a mass fingerprint similar to a mass fingerprint of *M. tuberculosis* Ag85B protein (Rv 1866c), and
(iv) a fourth polypeptide having a molecular weight of about 10 kDa, having a mass fingerprint similar to a mass fingerprint of *M. tuberculosis* CFP10 protein (Rv3874), and
(v) a fifth polypeptide having a molecular weight of about 6 kDa, having a mass fingerprint similar to a mass fingerprint of *M. tuberculosis* ESAT-6 protein (Rv3875).

Further, at least one of the following antigens of *Mycobacterium tuberculosis*, or fragment thereof, may be present in the agent of the invention: HSP70, 38 kDa protein and Ag85B. Also, one or more mycolic acids and/or a sugar-conjugated mycolate may be comprised in the agent, preferably trehalose dimycolate and/or a glycolipid, preferably lipoarabinomannan. The agent of the invention may additionally contain one or more salts or a solution thereof, and said salt is preferably sodium chloride.

Particularly in the case that the agent fulfils characteristic 2 above, i.e. is obtainable by cultivating the MTB-C strain and, homogenising the cell culture in the presence of a preferably non-ionic surfactant, the way by which it is obtainable may further be characterized as follows: (a) cultivating the MTB-C strain over a period equal or greater than three weeks and, subsequently, (b) homogenising the cell culture in the presence of a non-ionic surfactant. In a preferred embodiment, the method by which it is obtainable further comprises the steps:

a. separating the non-fragmented cells and the solubilised components by means of centrifugation,
b. subjecting the fraction of cell wall fragments to chemical or physical treatment to inactivate the eventual virulent strain cells that it eventually contains, and
c. drying the agent by lyophilisation.

The agent according to the invention may be preserved according to any method known in the art; however, for the case of a liposome formulation according to the invention, it is preferred that the preservation is by freeze-drying.

The present invention also relates to a pharmaceutical composition comprising the agent (liposome formulation) of the invention and a pharmaceutically acceptable carrier for use in prevention or therapy of an allergic response of a human or animal.

In a particular embodiment, the allergic response that may be treated by the agent (e.g. the liposome formulation) of the invention is IgE-mediated. The response may be atopy. The allergic response may be respiratory dysfunction and/or bronchovascular inflammation. Preferably the response is selected from asthma, hay fever, rhinitis and eczema. Without wishing to be bound to a particular theory, it is presently believed that asthma, hay fever, rhinitis and eczema can involve an allergenic response. The invention however relates to the all uses of the agent and pharmaceutical composition described herein for the use in prevention or therapy of any one or more of asthma, hay fever, rhinitis and eczema, irrespective of the question whether there is an allergic response underlying the asthma, hay fever, rhinitis and eczema in a particular individual. It is however preferred in one embodiment that the asthma is allergic asthma, and that rhinitis is allergic rhinitis. In a particular embodiment, the asthma is bronchial asthma.

The route of administration is not particularly limited as such, unless characteristics of the agent or composition so require. It is however preferred that the agent or composition of the invention is provided for injection, preferably subcutaneously or intramuscular, or for sublingual, inhaled, percutaneous or intradermal administration. In a particular embodiment, the agent or pharmaceutical composition of the invention is for administration of 200 μg or less per dose, and preferably up to 50 μg per dose, such as most preferably 25 μg per dose.

In a particular embodiment, the agent or pharmaceutical composition of the invention is for use in prevention of the allergic response. In an alternative particular embodiment, the agent or pharmaceutical composition of the invention is for use in therapy of the allergic response.

The agent according to the invention may be administered one or several times, and in the case of prevention, it is preferred to administer at least two times, preferably more than two times. The agent or pharmaceutical composition the invention may be provided for repeated administration, preferably in intervals of one week or more, and more preferably of two weeks or four weeks.

Shown in

Figure 14:
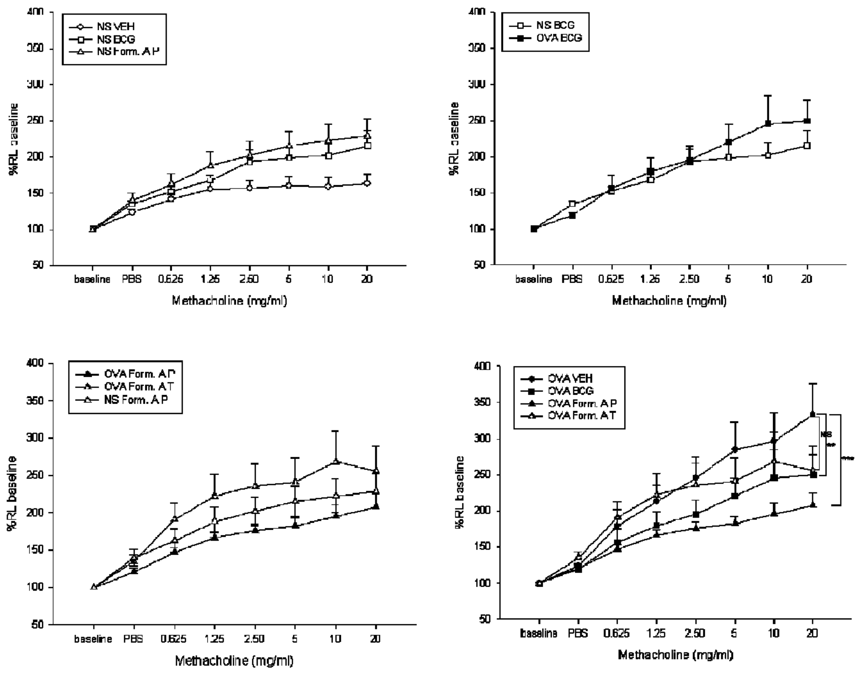

FIG. 14 are the normalized dose-response curves for each animal vis-à-vis its own response at baseline. Non-sensitized animals treated with BCG or FORMULATION A (P) exhibited higher reactivity versus non-sensitized animals in the untreated control group (upper left graph of FIG. 14). When comparing animals treated with the BCG vaccine, no differences in bronchial reactivity were observed between sensitized and non-sensitized animals (upper right graph of FIG. 14). In terms of treatment with the FORMULATION A vaccine, preventive administration (P) in sensitized animals resulted in lower reactivity than that exhibited by non-sensitized animals treated with the same vaccine (lower left graph of FIG. 14). Moreover, it was also below the reactivity seen both in sensitized animals and those treated with BCG (lower right graph of FIG. 14). When compared to the curve of the untreated sensitized mice, the inhibition of reactivity becomes very clear ($p<0.001$, ANOVA 2-factor), albeit without reaching the baseline reactivity values observed in non-sensitized mice. The therapeutic treatment regime slightly diminished the response to methacholine beginning at a dose of 2.50 mg/ml, though it never reached statistical significance (lower right graph of FIG. 14).

Figure 15:
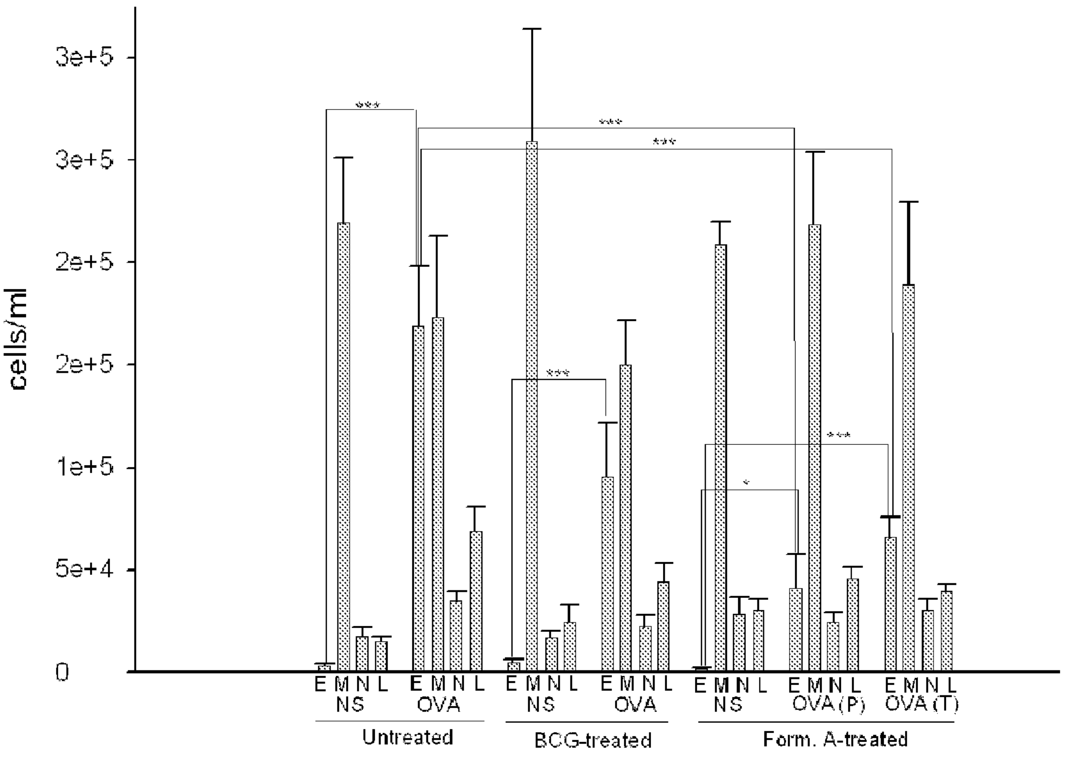

FIG. 15 charts the statistical significance of eosinophilia among the different groups. For more details, see the main text.

DEFINITIONS

"particle size" refers to, if not otherwise specified, the diameter of the particles. Where the particle size can not be determined exactly, the approximate particle size is meant.

"z-average" is the average particle size, determinable as described in the material and methods section.

ABBREVIATIONS

BAL bronchalveolar lavage
BCG *Bacillus* Calmette-Guérin
CFU Colony-forming unit
CpG cytosine-guanine dinucleotide(s)
DP Drug product
DS Drug substance
ELISA Enzyme-linked immunosorbent assay
ELISPOT Enzyme-linked immunospot assay
EMEA European Medicines Agency
FCMtb Fragments of a *Mycobacterium tuberculosis*-complex (MTB-C) strain
IFN-γ Interferon gamma
IgE Immunoglobulin E IGTIP Institut per a la Recerca en Ciències de la Salut Germans Trias i Pujol
IL Interleukin
IMP Investigational medicinal product
i.p. intraperitoneal
IPC In process controls
LCS Liposome concentrate suspension
LPS Lipopolysaccharide
Mtb *Mycobacterium tuberculosis*
Mtb-C *Mycobacterium tuberculosis*-complex
NCTC National Culture Type Collection (London)
OVA ovalbumin
PPD Protein-purified derivative
q.s. Quantum sufficit
s.c. subcutaneous
TB Tuberculosis
Th1 T helper cell 1
Th2 T helper cell 2
w/v weight/volume
w/w weight/weight
Form. A Formulation A

DETAILED DESCRIPTION OF THE INVENTION

The present invention relates to an agent comprising fragments of a *Mycobacterium tuberculosis*-complex (MTB-C) strain for use in prevention or therapy of an allergic response of a human or animal.

Unless expressly specified otherwise, the term "comprising" is used in the context of the present application to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

The detailed description discloses specific and/or preferred variants of the individual features of the invention. The present invention also contemplates as particularly preferred embodiments those embodiments, which are generated by combining two or more of the specific and/or preferred variants described for two or more of the features of the present invention.

The agent may further be characterized by at least one of the following characteristics:

1. The fragments originate from a virulent *Mycobacterium tuberculosis*-complex (MTB-C);
2. the agent is obtainable by cultivating the MTB-C strain and, subsequently, homogenising the cell culture in the presence of a preferably non-ionic surfactant.
3. the agent is a liposome formulation comprising fragments from a *Mycobacterium tuberculosis*-complex (MTB-C), a liposome forming agent and sucrose,
4. the agent is a liposome formulation comprising fragments from a *Mycobacterium tuberculosis*-complex (MTB-C), a liposome forming agent and having a z-average size of the particles of 150 nm or less.

Throughout the present specification, "virulent *Mycobacterium tuberculosis*-complex (MTB-C)" means a *Mycobacterium tuberculosis*-complex (MTB-C) strain that is virulent to (at least) humans. It is known that BCG (*M. bovis*), as well as heat-killed agents (such as heat-killed *M. vaccae*, which does not belong to MTB-C) are not virulent to immunocompetent humans. In the embodiment of the characteristic 1 above, the fragments do not originate from *M. bovis* or (heat-inactivated) *M. vaccae*. In a particular embodiment, the fragments do not originate from BCG, in particular not from BCG Danish 1331 Strain. For the avoidance of doubt, tuberculosis is not an allergic response. It is preferred that, within the constraints of this invention, the provided agent is not administered for the prevention or treatment of tuberculosis.

The agent according to characteristic 2 above may particularly be obtainable by a method comprising the steps: (a) cultivate the MTB-C strain over a period equal or greater than three weeks and, subsequently, (b) homogenate the cell culture in the presence of a non-ionic surfactant.

It can be recognized that characteristics 3 and 4 above have in common that the agent is a liposome formulation comprising fragments from a *Mycobacterium tuberculosis*-complex (MTB-C) and a liposome forming agent.

While each of the characteristics 1 to 4 above may be fulfilled alone, any one or more of them may also be fulfilled in combination. Thus, for example, also in the case of the characteristics 1 and 2, the agent may be in the form of a liposome formulation, and also in the case of the characteristics 1 to 3 the z-average size of the liposome particles may be 150 nm or less, and so on. Any combination of 2, 3 or all characteristics 1 to 4 is possible. It is generally accepted that a liposomation process generates a lipidic environment, facilitating the solubility and leading to a suspension of substances, such FCMtb. Liposomes within the meaning of this invention may be unilamellar, multilammellar or combinations thereof.

The fragments form a *Mycobacterium tuberculosis*-complex (MTB-C) strain are also termed FCMtb. FCMtb can be of any type of substance derived from the MTB-C strain, or from any mixture of MTB-C strains, whereby fragments being or derived from proteins and/or lipids are preferred. FCMtb within the sense of this application is typically a mixture of different protein antigens and lipids derivable from MTB-C cells. The cell fragments may be obtained by any method known to the person skilled in the art suitable for fragmenting microbial or bacterial cells, such as specifically MTB-C cells, for example homogenisation. In a particular embodiment, they can be obtained as described in WO2008053055 and EP2090318 A1, albeit not necessarily limited to a virulent strain, as described above.

The homogenisation can be carried out by means of ultrasound sonication, or by means of the use of small beads of approximately 0.1 mm in diameter, for example, silica or zirconia/silica beads, together with a mechanical homogenizer. A mechanical homogenizer that can be used, for example, is the BioSpec BeadBeater® model. The MTB-C cells are broken by means of this homogenisation process, so that small cell fragments, typically including small cell wall fragments, are obtained. In a particular embodiment, they can be obtained as described in WO2008053055 and EP2090318 A1, albeit not necessarily limited to a virulent strain, as described above.

A typically relevant feature of the manufacturing of the cell fragments is the "detoxification" of the cell wall fragments by partial delipidation, well known to the person skilled in the art, a process that allows removing the endotoxin-like molecules, like lipoarabinomanann. The FCMtb is therefore preferably detoxified and pasteurized, the obtained liposome formulation is then sterile and free of endotoxins. The dispersion of cell fragments in buffer can optionally be lyophilised to facilitate the storage thereof. To that end, the dispersion can be distributed into vials and lyophilised at a temperature between −15° C. and −120° C., such as for example −45° C. and with a vacuum, such as between 0.1 and 0.5 mbar.

When the agent is a liposome formulation, the liposomes usually have a size distribution in which at least 99.9% (by number) are smaller than 1 μm. In a particular embodiment, the z-average size of the particles, as determinable by dynamic light scattering, is 150 or less, preferably 135 nm or less, more preferably 125 nm or less. (Also possible are 145 nm or less, 140 nm or less, 130 nm or less, 120 nm or less, 110 nm or less, 100 nm or less, 95 nm or less, 90 nm or less, 85 nm or less, 80 nm or less). In dynamic light scattering the z-average parameter is considered a stable and important number obtainable by the technique, and the size number that is preferably used for quality control purposes. Preferably, the liposomes of the formulation according to this invention are monomodal, i.e. they show only one peak in dynamic light scattering measurements. More preferably, the liposomes of the formulation according to this invention are spherical, as can be tested by electron microscopy of freeze-fracturing preparations of the liposome formulation, as shown inFigure 8. Spherical thereby means that for at least 90% of the liposome particles (by number), all surface points of the individual particle have similar or identical distance to the centre of the liposome, i.e. the minimal radius of such a particle relates to the maximal radius of the same particle in a ration of 0.6 or more, 0.7 or more, 0.8 or more or 0.9 or more. The liposome formulation according to the present invention can comprise multilamellar or unilamellar liposomes, or a mixture thereof. In line with standard knowledge of the person skilled in the art, the dynamic light scattering measurements should be performed in a suitable buffer, i.e. a buffer which does not by itself cause disruption, disintegration or fusion of the liposomes or significantly destabilize them physically in any other way. As a rule of thumb, any buffer may be suitable as long as both ionic strength and pH value are comparable to the buffer in which the liposomes had been formed may be suitable. Preferably, a buffer of similar or identical composition to the buffer in which the liposomes had been formed, is used.

In the case of embodiment 3 above, the liposome formulation preferably comprises 1 to 20 (w/v) sucrose, preferably 2 to 12% (w/v) sucrose, more preferably 3 to 8% (w/v) sucrose, and most preferably 4 to 6% (w/v) sucrose. Approximately 5% sucrose are particularly preferred.

In one particular embodiment, the above-described liposome formulation has a z-average particle size in the range from 40 to 150 nm, preferably from 50 to 135 nm, and more preferably from 55 to 125 nm. (Also possible are 145 nm or less, 140 nm or less, 130 nm or less, 120 nm or less, 110 nm or less, 100 nm or less, 95 nm or less, 90 nm or less, 85 nm or less, 80 nm or less in combination with any of the lower values from the previous sentence). The z-average particle size is thereby (and in general for the size values throughout this specification) preferably measured by dynamic light scattering, as described in general above and in detail in the section "Materials and methods".

In an alternative particular embodiment, the z-average particle size of the above-described liposome formulation may be smaller, so that the liposome formulation is an emulsion, i.e. in this particular embodiment the z-average size of the particles is preferably below 40 nm.

It is preferred that the particle size is distributed evenly, so that the polydispersity index of the particles is 0.4 or less, preferably 0.3 or less.

Also the particles according to any of the characteristics 2 to 4 above may be further characterized in that the *Mycobacterium tuberculosis*-complex (MTB-C) strain is a virulent *Mycobacterium tuberculosis*-complex (MTB-C) strain. In a particular embodiment of the invention, the *Mycobacterium tuberculosis*-complex (MTB-C) strain used for the formulation according to the invention is the MTB-C strain NCTC 13536, deposited in 2010 at the NCTC in London.

In a preferred embodiment of any one or more of the above-described embodiments, the liposomes of the formulation according to this invention are furthermore monodisperse, which means that no significant width of the size distribution is observed. This is technically tested by a low polydispersity index (PDI) as determined by dynamic light scattering, such as 0.4 or less, preferably 0.3 or less. Hence, the liposome formulation is a liposome formulation, wherein the polydispersity index of the particles as determinable by dynamic light scattering is 0.4 or less, preferably 0.3 or less, and most preferably 0.25 or less.

The fragments from the *Mycobacterium tuberculosis*-complex (MTB-C) strain are obtainable by a process comprising an upstream process and a downstream process. In a particular embodiment, they can be obtained as described in WO2008053055 and EP2090318 A1, albeit not necessarily limited to a virulent strain, as described above. For illustrative purposes, the five main steps are briefly described here and particular modes of carrying out the process are given in Examples 2 and 3 below.

Upstream Process (Example 2):

Step 1: Culture of *Mycobacterium tuberculosis*

Step 2: Harvest of *Mycobacterium tuberculosis* and freezing of crude extract

Downstream Process (Example 3):

Step 3: Cell fragmentation and delipidation

Step 4: Pasteurization

Step 5: Freeze-drying (optional)

In a more preferred embodiment of any of the above-described embodiments, the *Mycobacterium tuberculosis*-complex (MTB-C) strain is a virulent *Mycobacterium tuberculosis*-complex (MTB-C) strain. Virulent refers to the pathogenicity by case and/or the ability of the bacilli to invade the tissues of the (human) host and to cause active disease. The virulent strain can be any virulent strain of any of the species belonging to MTB-C, but a strain belonging to *M. tuberculosis* is preferred. The MTB-C strain according to this invention may be cultivated by inoculation in culture media well-known by the person skilled in the art, for example Middlebrook 7H10 or 7H11 agar, Sauton's medium or Proskauer-Beck medium. The culture of the virulent strain is preferably performed over an extended time period, such as, for example, a period equal to or greater than three weeks, preferably comprised between 3 and 4 weeks. The temperature of the culture is preferably maintained between 34° C. and 38° C. Once the culture ends, the cells are harvested and isolated using techniques well known in the art, such as those described in patent application ES2231037-A1.

The liposome forming agent of the liposome formulation is preferably a hydrogenated, partially hydrogenated or non-hydrogenated phospholipid. The phospholipid used can be or comprise, for example: phosphatidylcholine, phosphatidylserine and phosphatidyl-inositol. Most typical is phosphatidylcholine, which can be synthesized or isolated from a variety of natural sources. Preferably the liposome forming agent is or comprises lecithin, selected from the group consisting of egg lecithin and soy lecithin. Soy lecithin is a complex mixture of phospholipids including inter alia phosphatidylcholine, and is particularly preferred. Typical lipids which may also be comprised in the formulation, either as liposome forming agent itself, or as further component, are: dicetyl phosphate (DCP), dimyristoyl phosphatidylcholine (DMPC), dimyristoyl phosphatidylglycerol (DMPG), dioleoyl phosphatidylcholine (DOPc), dioleoyl phosphatidylethanolamine (DOPE), dioleoyl phosphatidylserine (DOPS), dipalmitoyl phosphatidylcholine (DPPC), dipalmitoyl phosphatidylglycerol (DPPG), phosphatidylcholine (PC) and/or phosphatidylserine (PS), whereby the respective lipid may be hydrogenated, partially hydrogenated or non-hydrogenated. The liposomes can be formed using conventional auxiliary lipids and techniques well-known by the person skilled in the art, such as those described in the patent application ES2231037-A1.

It is further preferred that in any of the embodiments described above, the ratio of (a): the fragments from a *Mycobacterium tuberculosis*-complex (MTB-C) strain and (b) the liposome forming agent, is between 0.01:1 and 1:1, preferably between 0.06:1 and 0.1:1.

In a more preferred embodiment of any of the above-described, the liposome formulation additionally comprises: (d) a tensioactive agent. Generally, all types of agents capable of changing the value of surface tension may be used as tensioactive agent in the sense of this invention, but excluded are compounds which fall under the definition of the liposome-forming agent given above. Various types of tensioactive agents are known to the person skilled in the art and may be used in the liposome formulation according to the present invention. As is known to the skilled person, tensioactive agents are generally chemicals with a polar-nonpolar structure. Without wishing to be limited to any particular theory, tensioactive agents generally have the tendency to locate to the surface of particles, thereby creating a monomolecular layer on the interface that reduces the surface tension value. Tensioactive agents are also referred to as surfactants or active surface agents. In a preferred embodiment of the surfactant-containing liposome formulation, the tensioactive agent is selected from sterols and derivatives thereof, such as cholesterol, and/or bile salts or derivatives thereof, such as cholate. Particularly preferred embodiments are those wherein the tensioacive agent is selected from cholate, deoxycholate, cholesterol and cholesterol hemisuccinate. A good, but not limiting mode of carrying out the invention is where the liposomes of the formulation comprise both soy-derived lecithin and sodium cholate.

In an even more preferred embodiment, the liposome formulation comprising (d) the tensioactive agent, is a liposome formulation, wherein the ratio between (a) and (d) is between 0.05:1 and 3:5 (w/w). Various types of liposome forming agents may be used, as are well known to the person skilled in the art.

The agent can optionally contain additives improving the stability, for example: vitamin E, which is believed to act as a lipid antioxidant and thus particularly useful in the case of liposomes.

In a more preferred embodiment, the liposome formulation described above is a liposome formulation, wherein the fragments of MTB-C cells are or comprise cell wall fragments. Any strain belonging to MTBC, and preferably any strain belonging to *Mycobacterium tuberculosis*, may be used. In another more preferred embodiment, the liposome formulation described above comprises fragments of the MTB-C strain NCTC 13536, which was deposited in 2010 at the NCTC in London (Example 1). Another strain which may be used, and fragments of which may therefore be comprised in the liposome formulation, is called H37Rv, which, for example, can be obtained from the National Collection of Type Cultures (NCTC), London, Great Britain (deposit number NC007416) and is often used by researchers in this field. It is also possible that more than one strain be used, i.e. that the liposome formulation comprises fragments of various, such as two, three, or more than three strains.

The agent of the invention may also additionally comprise one or more non-ionic surfactants (e). The non-ionic surfactant may be preferably selected from the group consisting of alkylphenol ethoxylates, sorbitan ester ethoxylates, and more preferably a octylphenol ethoxylate. This surfactant may also be used in the case of characteristic 2 above.

The fragments of MTB-C of the agent of the invention may also be or comprise cell wall fragments.

The liposome forming agent of the liposome formulation is preferably a hydrogenated, partially hydrogenated or non-hydrogenated phospholipid. The phospholipid used can be or comprise, for example: phosphatidylcholine, phosphatidylserine and phosphatidyl-inositol. Most typical is phosphatidylcholine, which can be synthesized or isolated from a variety of natural sources. Preferably the liposome forming agent is or comprises lecithin, selected from the group consisting of egg lecithin and soy lecithin. Soy lecithin is a complex mixture of phospholipids including inter alia phosphatidylcholine, and is particularly preferred. Typical lipids which may also be comprised in the formulation, either as liposome forming agent itself, or as further component, are: dicetyl phosphate (DCP), dimyristoyl phosphatidylcholine (DMPC), dimyristoyl phosphatidylglycerol (DMPG), dioleoyl phosphatidylcholine (DOPc), dioleoyl phosphatidylethanolamine (DOPE), dioleoyl phosphatidylserine (DOPS), dipalmitoyl phosphatidylcholine (DPPC), dipalmitoyl phosphatidylglycerol (DPPG), phosphatidylcholine (PC) and/or phosphatidylserine (PS), whereby the respective lipid may be hydrogenated, partially hydrogenated or non-hydrogenated. The liposomes can be formed using conventional auxiliary lipids and techniques well-known by the person skilled in the art, such as those described in the patent application ES2231037-A1.

It is further preferred that in any of the embodiments described above, the ratio of (a): the fragments from a *Mycobacterium tuberculosis*-complex (MTB-C) strain and (b) the liposome forming agent, is between 0.01:1 and 1:1, preferably between 0.06:1 and 0.1:1.

In a more preferred embodiment of any of the above-described, the liposome formulation additionally comprises: (d) a tensioactive agent. Generally, all types of agents capable of changing the value of surface tension may be used as tensioactive agent in the sense of this invention, but excluded are compounds which fall under the definition of the liposome-forming agent given above. Various types of tensioactive agents are known to the person skilled in the art and may be used in the liposome formulation according to the present invention. As is known to the skilled person, tensioactive agents are generally chemicals with a polar-nonpolar structure. Without wishing to be limited to any particular theory, tensioactive agents generally have the tendency to locate to the surface of particles, thereby creating a monomolecular layer on the interface that reduces the surface tension value. Tensioactive agents are also referred to as surfactants or active surface agents. In a preferred embodiment of the surfactant-containing liposome formulation, the tensioactive agent is selected from sterols and derivatives thereof, such as cholesterol, and/or bile salts or derivatives thereof, such as cholate. Particularly preferred embodiments are those wherein the tensioacive agent is selected from cholate, deoxycholate, cholesterol and cholesterol hemisuccinate. A good, but not limiting mode of carrying out the invention is where the liposomes of the formulation comprise both soy-derived lecithin and sodium cholate.

In an even more preferred embodiment, the liposome formulation comprising (d) the tensioactive agent, is a liposome formulation, wherein the ratio between (a) and (d) is between 0.05:1 and 3:5 (w/w). Various types of liposome forming agents may be used, as are well known to the person skilled in the art.

The liposomes can optionally contain additives improving their stability, for example: vitamin E, which is believed to act as a lipid antioxidant.

In a more preferred embodiment, the liposome formulation described above is a liposome formulation, wherein the fragments of MTB-C cells are or comprise cell wall fragments.

Any strain belonging to MTBC, and preferably any strain belonging to *Mycobacterium tuberculosis*, may be used. In another more preferred embodiment, the liposome formulation described above comprises fragments of the MTB-C strain NCTC 13536, which was deposited in 2010 at the NCTC in London (Example 1). Another strain which may be used, and fragments of which may therefore be comprised in the liposome formulation, is called H37Rv, which, for example, can be obtained from the National Collection of Type Cultures (NCTC), London, Great Britain (deposit number NC007416) and is often used by researchers in this field. It is also possible that more than one strain be used, i.e. that the liposome formulation comprises fragments of various, such as two, three, or more than three strains.

Considering the approximately 4000 putative antigens of *M. tuberculosis*, it is impossible to analyse drug substance for all of these proteins. Nevertheless, certain MTB-C proteins have been shown to be relevant for the desired immune response. These are five protein bands have approximate sizes of 6, 10, 30, 38, and 70 kDa (Renshaw, et al., 2005, EMBO Journal 24(14):2491-2498; Singh, et al., 2005, Clin. Diagn. Lab. Immunol. 12(2), 354-358). Therefore, in an even more preferred embodiment, the liposome formulation described above comprises at least two, preferably three, more preferably four, and most preferably all of the following:

(i) a first polypeptide having a molecular weight of about 70 kDa as measured following electrophoresis on a sodium dodecylsulfate (SDS) polyacrylamide gel, wherein the first polypeptide has a mass fingerprint similar to a mass fingerprint of *M. tuberculosis* HSP70 protein (Rv0350), (ii) a second polypeptide having a molecular weight of about 38 kDa as measured following electrophoresis on a sodium dodecylsulfate (SDS) polyacrylamide gel, wherein the second polypeptide has a mass fingerprint similar to a mass fingerprint of *M. tuberculosis* 38 kDa protein (Rv 0934), (iii) a third polypeptide having a molecular weight of about 30 kDa as measured following electrophoresis on a sodium dodecylsulfate (SDS) polyacrylamide gel, wherein the third polypeptide has a mass fingerprint similar to a mass fingerprint of *M. tuberculosis* Ag85B protein (Rv 1866c), and (iv) a fourth polypeptide having a molecular weight of about 10 kDa as measured following electrophoresis on a sodium dodecylsulfate (SDS) polyacrylamide gel, wherein the fourth polypeptide has a mass fingerprint similar to a mass fingerprint of *M. tuberculosis* CFP10 protein (Rv3874), and (v) a fifth polypeptide having a molecular weight of about 6 kDa as measured following electrophoresis on a sodium dodecylsulfate (SDS) polyacrylamide gel, wherein the fifth polypeptide has a mass fingerprint similar to a mass fingerprint of *M. tuberculosis* ESAT-6 protein (Rv3875).

In a yet more preferred embodiment thereof, the liposome formulation further comprises a lipopolypeptide having a molecular weight of about 19 kDa as measured following electrophoresis on a sodium dodecylsulfate (SDS) polyacrylamide gel, wherein the lipopolypeptide has a mass fingerprint similar to a mass fingerprint of *M. tuberculosis* 19 kDa lipoprotein antigen precursor LpqH (Rv 3763). The respective band can be visualized by methods known in the art, such as silver staining. The researchers of the present invention surprisingly found, in preclinical animal models of *M. tuberculosis* infection vaccinated with MTB-C strain, that the total IgG humoral response against this polypeptide may be the highest among all antigens in the formulation.

Non-limiting examples of how the polypeptides or lipopolypeptides may be identified are given in Example 4.

Even more preferably, the liposome formulation described above is further characterized in that at least one of the following antigens of *Mycobacterium tuberculosis*, or fragment thereof, is present: HSP70, 38 kDa protein, Ag85B, and most preferably at least one of HSP70, 38 kDa protein and Ag85B. Fragment in this sense is any part, such as for example a degradation product, of any of these polypeptides. Various ways of obtaining such fragments are possible, for example chemical or enzymatic hydrolysis, whereby it is not relevant if the fragmentation had occurred purposely or not, prior to liposome formation or thereafter. It is preferred that the respective fragment can be assigned to its respective origin, such as, for example, by substantial overlap in amino acid sequence, such as at least 5, at least 10, at least 20 consecutive amino acids.

The fragments according to the present invention are preferably obtained from bacilli grown under the stressful conditions of starvation, low oxygen and low pH. Low oxygen is due to the confluent growth of the bacteria on plates which are closed in hermetic bags during the growth period, which is for example 21 days, which leads to a microaerobiotic environment. The low pH is explained as follows: At the beginning of culture the pH value is 7.0-6.8, and the end, after typically 21 day of culture, the pH value is 6.4-6.5). Under these conditions, the metabolism of the bacteria is slower, which leads to stationary growth. It is understood that this renders the bacilli more resistant to stress. Under such conditions presumably cultured bacilli develop similar characteristics as in vivo latent bacilli in LTBI (Latent tuberculosis infection). The antigens present in FCMtb are thus expected to trigger a new immunological response against antigens of the latent bacilli, i.e. the so-called “structural” antigens as well as those associated to stress responses.

Mycobacterial glycolipids have long been recognized to have immunomodulatory activity, notably the induction of granulomatous responses and to exert potent adjuvant-like effects. Therefore, in a more preferred embodiment, the liposome formulation described above contains lipids which are typically found in *Mycobacterium tuberculosis*, or derivatives thereof, such as conjugation products like sugar conjugated lipids. Several immunogenic lipid components have been identified in *M. tuberculosis* samples (Brennan, Tuberculosis (Edinburgh), 2003, 83(1-3), 91-97) and analytical methods for their determination have been developed (electrophoresis, SDS-PAGE, thin layer chromatography). Although the isolation of each lipid component would require such an aggressive treatment that quantitative data or percentages of each component detectable in the MTB-C extract or in the liposome formulation are difficult to obtain, the qualitative characterisation shall serve to characterize a further preferred embodiment of this invention. According to this further preferred embodiment, one or more of mycolic acids, preferably belonging to any one or more of types I, III or IV is comprised. Alternatively or in addition, a sugar-conjugated mycolate, preferably trehalose dimycolate may be comprised in the formulation. Alternatively or in addition, a glycolipid lipoarabinomannan (LAM) may be comprised in the formulation. Furthermore the multiantigenic nature of the fragments (multiantigenic protein mixture plus lipids, instead of purified antigens alone) is believed to be an advantage and therefore the cell fragmentation process can be adapted by the skilled person so as to allow the optimal cellular antigen mixture.

Homogenisation of the MTB-C cells is carried out in the presence of one or more surfactants, preferably a nonionic surfactant. Hence, the liposome formulation described above may additionally comprise one or more such surfactants. A large number of such surfactants are within the standard knowledge of a person skilled in the art. Preferably, the nonionic surfactant used is selected from the group consisting of alkylphenol ethoxylates, and sorbitan ester ethoxylates. More preferably, the nonionic surfactant is selected from the group of octylphenol ethoxylates. Even more preferably, octylphenol ethoxylates with an ethylene oxide content comprised between 7 and 8 moles are used, which surfactants can be found on the market under the name Triton X-114®. The homogenised mass containing the cell wall fragments is subjected to a conventional treatment to separate and reject the non-fragmented cells and the solubilised components. Centrifugation at different speeds and washing with buffer solution as described in patent application ES2231037-A1 can be used for example. Sediment containing the cell wall fragments is obtained after performing the mentioned purification processes. Said sediment is dispersed in phosphate-buffered saline (PBS) buffer and is subjected to a conventional treatment to ensure the complete inactivation of the MTB-C cells which may have remained viable after the fragmentation and purification process. The mentioned treatment can be a chemical process, for example by means of treatment with formaldehyde, or a physical process, for example by means of autoclaving or pasteurisation treatment. Examples of lipid characterization are given in Example 5 below. The agent of the invention may additionally contain one or more salts or a solution thereof, and said salt is preferably sodium chloride.

Particularly in the case that the agent fulfils characteristic 2 above, i.e. is obtainable by cultivating the MTB-C strain and, homogenising the cell culture in the presence of a preferably non-ionic surfactant, the way by which it is obtainable may further be characterized as follows: (a) cultivating the MTB-C strain over a period equal or greater than three weeks and, subsequently, (b) homogenising the cell culture in the presence of a non-ionic surfactant. In a preferred embodiments, the method by which it is obtainable further comprises the steps:

d. separating the non-fragmented cells and the solubilised components by means of centrifugation,
e. subjecting the fraction of cell wall fragments to chemical or physical treatment to inactivate the eventual virulent strain cells that it eventually contains, and
f. drying the agent by lyophilisation.

The process may be performed as described in EP2090318 A1.

The agent according to the invention may be preserved according to any method known in the art; however, for the case of a liposome formulation according to the invention, it is preferred that the preservation is by freeze-drying.

In an even more preferred embodiment of any of the above, the liposome formulation is freeze-dried. The liposomes can be subjected to lyophilisation to thus obtain the immunotherapeutic agent in the form of lyophilised liposomes. To that end, the dispersion can be distributed into vials and lyophilised at a low temperature, such as between −15° C. and −120° C., such as for example −45° C. and with a vacuum, such as between 0.1 and 0.5 mbar. The vials obtained after lyophilisation contain the liposome formulation suitable as immunotherapeutic agent and they are preferably stored at very low temperatures, for example at −70° C.

The invention also provides a suspension, wherein the liposome formulation of any of the preceding claims is reconstituted in a solvent. In a preferred embodiment, the solvent of this suspension is aqueous, more preferably and most preferably is or comprises physiological serum. Methods of suspending liposome formulations in a solvent are well known to the person skilled in the art. It is a particularly advantageous property of the formulation according to this invention that it can be suspended faster than conventional liposome formulations comprising MTB-C fragments (see Example 9)

A further object of the invention is the provision of a pharmaceutical composition comprising the agent of the invention for use in prevention or therapy of an allergic response of a human or animal, whereby the agent is or comprises the agent described above in any of the embodiments described or combinations thereof. The main scope of the pharmaceutical formulation/galenic formulation of the drug substance is to obtain a suspension effective and stable enough to be well recognized by the cells and which has the potential to trigger a relevant cellular immune response in a human or animal body. To that end, the invention also provides a pharmaceutical composition comprising the liposome formulation, or the suspension as described in any one or more of the embodiments described above, and a pharmaceutically acceptable carrier, excipient or diluent. Various such carriers, excipients and diluents are known to the person skilled in the art, and they are in no way limited by this disclosure. Rather, any substance suitable as carrier, excipient or diluent may be used. In a preferred embodiment, this pharmaceutical composition additionally comprises a pharmaceutically acceptable adjuvant. Adjuvant is thereby to be understood as a substance comprised in this embodiment of the invention, whereby the adjuvant is a substance capable of stimulating the immune system when applied to a human or animal body in response to the target antigen, whereby the adjuvant does not itself confer immunity. Without wishing to be limited to any particular adjuvant substance, preferred embodiments are wherein the adjuvant is an aluminium salt, such as aluminium chloride, or a mineral oil or a composition comprising mineral oil, such as incomplete Freund's adjuvant (IFA) or complete Freund's adjuvant (CFA), or an ammonium halogenide, such as an alkylated ammonium bromide, such as dimethyldioctadecylammonium bromide.

A particular agent of the invention for the treatment of the invention is developed by ARCHIVEL FARMA (Spain) and termed Formulation A. Its preparation is described in the section "Preferred mode of carrying out the invention"

These applications are supported by the results the inventors have obtained in a mouse model of allergy-induced asthma, as detailed below in the examples. Briefly, mice were sensitized to ovalbumin (OVA) by intraperitoneal injection with OVA followed by local exposure to nebulized antigen (i.n.). Sensitized mice were divided into groups—untreated and those treated with the test vaccine, BCG (positive control) or vehicle—all administered subcutaneously (s.c.). The inventors also established control groups of the mentioned treatments in non sensitized mice. Increased bronchial reactivity in response to methacholine, as well as the presence of peribronchial eosinophils in those animals exposed to OVA (but not treated), indicated that the allergic process was efficiently induced. BCG vaccination reduced, by almost half, the levels of inflammation (not significant) and bronchial hyper-responsiveness (without reverting to baseline levels). Administration of the FORMULATION A vaccine as a preventive measure greatly reduced pulmonary eosinophilia and reversed nearly to baseline bronchial hyperreactivity levels. Use of the FORMULATION A vaccine as a therapeutic agent significantly decreased bronchovascular inflammation, while a tendency towards decreased bronchial hyperresponsiveness in response to the OVA antigen was observed. Based on these results, the inventors conclude that when the FORMULATION A vaccine is administered 3 times before the challenge phase, it has a clearly beneficial effect on the airways of OVA-challenged mice, while its therapeutic administration clearly reduces inflammation and has a mild effect on bronchial hyperresponsiveness.

In a particular embodiment, the allergic response that may be treated by the agent (liposome formulation) of the invention is IgE-mediated. IgEs are allergy-associated immunoglobulins secreted by B cells, and the switching of B-cells towards IgE production is typically induced by Th2 cytokines. It is thus desirable in one aspect of the invention that the no increased isotype switching towards IgE occurs and/or that no Th2 response is triggered.

The response may be atopy. The allergic response may be respiratory dysfunction and/or bronchovascular inflammation. Preferably the response is selected from asthma, hay fever, rhinitis and eczema. Without wishing to be bound to a particular theory, it is presently believed that asthma, hay fever, rhinitis and eczema can involve an allergenic response. The invention however relates to the all uses of the agent and pharmaceutical composition described herein for the use in prevention or therapy of any one or more of asthma, hay fever and eczema, irrespective of the question whether there is an allergic response underlying the asthma, hay fever, rhinitis and eczema in a particular individual. It is however preferred in one embodiment that the asthma is allergic asthma. In a particular embodiment, the asthma is bronchial asthma. The agent of the present invention is also for the treatment or prevention of multiple allergies. Multiple allergies is a condition in which multiple allergic reactions, such as any two or more of the following asthma, eczema and allergic rhinitis occur together. Rhinitis an irritation/inflammation of the mucous membrane inside the nose. Symptoms of rhinitis are a stuffy nose, runny nose, and post-nasal drip. The most common kind of rhinitis is allergic rhinitis, may cause additional symptoms, such as sneezing and nasal itching, coughing, fatigue.

The route of administration is not particularly limited as such, unless characteristics of the agent or composition so require. The drug can be administered in a mucosa, for example, ocular, intranasal, oral, gastric, intestinal, vaginal, or urinary tract mucosa, or parenterally, for example, subcutaneously, intradermally, percutaneously, intramuscularly, intravenously, or intraperitoneally or by inhalation. Parenteral administration may be preferred in some embodiments. In a particular embodiment, the invention provides this liposome formulation, suspension or pharmaceutical composition for injection. It is preferred that the agent or composition of the invention is provided for injection, preferably subcutaneously or intramuscular, or for sublingual administration or for inhaled administration.

The suitable dose of the liposome formulation, suspension or pharmaceutical composition according to what is described above in relation to the use thereof in a method of treatment of the human body by therapy depends on several parameters, including the method of administration and the subject to be treated. In a preferred embodiment, it is for administration to the human body. In a preferred embodiment thereof, this occurs in a dose comprising 1 to 1000, preferably 3 to 250. In a particular embodiment, the agent or pharmaceutical composition of the invention is for administration of 200 μg or less per dose, and preferably about 5 to 50 μg FCMtb per dose, such as most preferably 25 μg FCMtb per dose.

In a particular embodiment, the agent or pharmaceutical composition of the invention is for use in prevention of the allergic response. Preventive medicine or preventive care refers to measures taken to prevent diseases, rather than curing them or treating their symptoms. Preventive care may include examinations and screening tests tailored to an individual's age, health, and family history. A prophylactic treatment may be administered. Prophylaxis is any procedure whose purpose is to prevent, rather than treat or cure a disease. Prophylactic measures can be subdivided in primary prophylaxis (to prevent the development of a disease) and secondary prophylaxis (whereby the disease has already developed and the patient is protected against worsening of this process). Sometimes, prevention is sub-divided in universal prevention, selective prevention and indicated prevention. Universal prevention Involves whole population (nation, local community, school, district) and aims to prevent the condition. It is intended that all individuals are subjected to the treatment. Selective prevention involves groups whose risk of developing an allergic reaction like allergic asthma is above average. The groups may be distinguished by traits such as age (e.g. children), or family history. Indicated prevention involves a screening process, and aims to identify individuals who exhibit early signs of the allergic reaction. All types of prevention/therapy are covered by the invention, although a subset may be selected in some embodiments thereof.

In an alternative particular embodiment, the agent or pharmaceutical composition of the invention is for use in therapy of the allergic response. Therapy or curative care is generally the treatment of an individual showing symptoms of the allergic reaction. Thus, curative care differs from preventive care, which aims at preventing the appearance of the condition, and from palliative care, which concentrates on reducing the severity of disease symptoms, such as pain.

The inventors have provided evidence (see examples) that the agent of the prevention is highly efficient for both therapeutic and preventive purposes.

The agent according to the invention may be administered one or several times, and in the case of prevention, it is preferred to administer at least two times, preferably more than two times. The agent or pharmaceutical composition the invention may be provided for repeated administration, preferably in intervals of one week or more, and more preferably of two weeks or four weeks.

In a particular embodiment, the agent or pharmaceutical composition of the invention is for administration to individuals suffering from or being prone to the development of the respective allergic reaction, including asthma and/or for individuals having a respective predisposition or being suspect of having a respective predisposition. Individuals suspect of having a respective predisposition may be for example family members, particularly children, from families wherein allergic reactions are known, such as from one or both parents or from (older) siblings. The goal of any family prone to allergies is to prevent the development of allergies in their child. To this end, the agent of the present invention may be administered as a preventive measure.

The present disclosure further provides the MTB-C strain NCTC 13536, deposited in 2010 at the NCTC in London. The strain has a low genetic polymorphism. Therefore, the agent comprising fragments of NCTC 13536 has the advantage of very high reproducibility because of the low genetic polymorphism.

PREFERRED MODE OF CARRYING OUT THE INVENTION

In one particular embodiment, it is preferred that formulation A as described herein is a particular agent to be used according to the invention. Formulation A is characterized as follows. When the dose is 50 μg FCMtb, the amounts/substances given in Table 1 are present in one vial of the formulation:

TABLE 1

| COMPONENTS | UNIT PER VIAL | FUNCTION |
|---|---|---|
| | DRUG SUBSTANCE | |
| FCMtb | 66.7 mg | Immunogen |
| | Further components | |
| Sucrose | 20,000.0 mg | Charge substance (freeze-drying) and cryoprotector |
| Soy lecithin [1] | 845.8 mg | Liposome forming agent |
| Sodium cholate | 92.0 mg | Tensioactive |
| Sodium chloride [2] | 20.8 mg | Solvent |
| | Particle characterization | |
| z-average particle size | 75 +/− 20 nm | |
| Polydispersity index | ≤0.350 | |

[1] Containing Phosphatidylcholine (94.0% (w/w))

[2] Added as NaCl 0.9% solution.

A liposome formulation made of soy lecithin (liposome forming agent) highly enriched with phosphatidylcholine (94.0% (w/w)) and sodium cholate (tensoactive agent) has shown to be adequate to guarantee greater solubility of the drug substance during manufacture as well as in the reconstituted suspension. One important parameter for stability of the FCMtb in the liposome formulation is the proportion of the components which constitute the liposome. After testing different ratios of FCMtb/lipid component, it was established that a very good ratio is approximately 0.03:0.2:0.7 (FCMtb:sodium cholate:soy lecithin, w/w/w). It was further observed that the liposome formation was enhanced by the presence of salts in the aqueous phase. Therefore, sodium chloride is included in this particular formulation.

TABLE 2

Drug product (FCMtb) at 50 ug/dose, measured after reconstitution of the lyophilized liposome composition

| Parameter | | Acceptance criteria | Test methods |
|---|---|---|---|
| Appearance | | White to off-white powder | Visual inspection |
| Cake morphology | | Flat to almost flat and homogeneous | Visual inspection |
| Dosage uniformity | Mass uniformity (mg/vial) | 21.02 ± 15% | Weighing, in house method |
| | Mass mean (mg/vial) | Mass ± 5% | Weighing, in house method |
| Water content (%) | | ≤3% | Karl Fischer coulometric assay, Ph. Eur. 2.5.12 (USP<921>) |
| Total protein content of FCMtb | | 90-140 μg/mg FCMtb | BCA assay, Ph. Eur. 2.5.33 (USP<1057>) |
| Time to reconstitution (s) | | Well reconstituted ≤10 s | Visual inspection |
| pH | | 7-8 | Potentiometry, Ph. Eur 2.2.3 (USP<791>) |
| Particle size | z-average (nm) (Polydispersity index[3]) | 75 ± 20 (≤0.310) | Dynamic light scattering Ph. Eur. 2.9.31 |
| Immunogenic potency in *M. Tuberculosis* infected murine model | Antigen-specific IFN-γ Spot forming units PPD | 3-12 Ratio SFU/$10^6$ cells with respect to basal value (Basal value in SFU/$10^6$ cells) | ELISpot |
| Protein profile | SDS-PAGE | Positive for bands: 70, 38, 30, 10, 6 kDa | Electrophoresis by SDS-PAGE |
| | Western-blot | Positive for HSP70 (Rv0350), 38 kDa (Rv0934), Ag85B (Rv1886c) | Western-blot |
| Sterility | | Sterile | Ph. Eur. 2.6.1 (USP<71>) |
| Bacterial endotixins (IU/dose) | | ≤10 IU/vial | Ph. Eur. 2.6.14 method D (USP<85>) |

In a preferred mode the invention is carried out such that the liposome formulation according to this invention has the properties according to Table 2.

For administration to subjects, the vial can be reconstituted with 0.4 ml of water for injections to give a suspension containing 166.7 μg/ml of FCMtb.

Table 3 shows the concentration of each component per vial after reconstitution at 50 μg/dose.

TABLE 3

Concentration of components after reconstitution in 0.4 mL water for injection.

| Components | Concentration per mL |
|---|---|
| DRUG SUBSTANCE | |
| FCMtb | 166.7 mg/mL |
| EXCIPIENTS | |
| Sucrose | 50,000.0 μg/mL |
| Soy lecithin | 2,114.4 mg/mL |
| Sodium cholate | 230.0 mg/mL |
| Sodium chloride | 52.1 mg/mL |

It is preferred that this formulation is administered for prevention or therapy of an allergic response, including asthma and rhinitis.

MATERIAL AND METHODS

To evaluate in vivo the possible therapeutic benefit of the agent according to the present invention, the agent FORMULATION A, produced by ARCHIVEL FARMA, was administered under two different protocols for the treatment of allergy-mediated respiratory problems in mice.

Reference Materials a) Monoclonal antibodies: Specific monoclonal antibodies (anti-HSP70, anti-38 kDa, anti-Ag85B, (from Lionex Diagnostic GmbH, Braunschweig, Germany)) are used for the identification of the protein profile of FCMtb batches.

b) Albumin Standard: This standard, used for the determination of protein content, is composed of bovine albumin in 0.9% of saline solution (2 mg/ml), conserved in sodium azide (manufacturer: Pierce).

c) Trehalose 6,6'-dimicolate from *Mycobacterium tuberculosis* (TDM) standard: Commercially available TDM (Sigma) is used for the identification of TDM of FCMtb batches.

d) Mycolic acids from *Mycobacterium tuberculosis* standard A commercially available mycolic acid (Sigma) is used for the identification of mycolic acid of FCMtb batches.

e) Molecular weight marker: A commercially available molecular weight marker named SeeBlue® Plus pre-stained Standard" (Invitrogen) is used.

Determination of Parameters a) pH

The pH of the reconstituted suspension of FCMtb (20 mg/ml) is determined by potentiometry according to Ph. Eur. 2.2.3 and USP<791>.

b) Water Content

The test for the determination of residual water of the lyophilized FCMtb is carried out using Coulometric Karl Fisher equipment, and it follows the general indications of the Ph. Eur., method 2.5.12, and USP <921> Water determination.

c) Determination of Total Protein Content

The test for the determination of total protein content of the FCMtb is carried out using a commercial kit (BCA kit, Pierce) and following Ph. Eur., method 2.5.33, method 4 (Bicinchoninic acid or BCA assay) and USP <1057>.

d) Identification of Protein Profile by Sodium Dodecyl Sulphate Polyacrylamide Gel Electrophoresis (SDS-PAGE)

The test is performed according to Ph. Eur., method 2.2.31 and USP <726>; the detection of proteins in the gel is performed by an adapted Coomassie staining or by Silver staining. Test samples: Reconstitute FCMtb in purified water at 40 or 20 mg/ml concentration. Reference solutions: Molecular weight marker, Purified antigens, FCMtb reference standard

TABLE 4

| Reference antigens Purified Antigens |
|---|
| *M. tuberculosis* HSP70 protein (Rv 0350) |
| *M. tuberculosis* 38 KDa protein (Rv0934) |
| *M. tuberculosis* Ag85B protein (Rv1886c) |
| *M. tuberculosis* 19 kDa protein (Rv 3763) |
| *M. tuberculosis* CFP10 protein (Rv3874) |
| *M. tuberculosis* ESAT6 protein (Rv3875) |

For Coomassie staining, Gel-Code Blue Stain reagent solution (Pierce) is used according to the manufacturer's instructions. For Silver Staining, the PROTSIL1 Kit from Invitrogen is used according to the manufacturer's instructions. For Western Blot analysis, proteins are separated by SDS PAGE according to standard methods known in the art and then electrophoretically transferred onto a PVDF membrane for immunodetection using specific monoclonal antibodies. The interaction antigen-antibody is visualized by incubation with an anti-antibody which triggers a chemiluminescent reaction. Antigens from Lionex (Braunschweig, Germany) (*M. tuberculosis* HSP70 protein (70 kDa), *M. tuberculosis* 38 kDa protein, *M. tuberculosis* Ag85B protein (30 kDa), and specific monoclonal antibodies anti-HSP70, anti-38 kDa, and anti-Ag85B from Lionex are used.

e) Identification of Mycolic Acids

Mycolic acids in FCMtb are examined by one-dimensional TLC, following the Ph. Eur., method 2.2.27. Test samples: Lyophilised FCMtb, 40 mg. Reference solutions: Mycolic acid standard (Sigma). Procedure:

a) Extraction process: The sample is extracted with chloroform:methanol (1:1) and then it is incubated overnight. The supernatant fraction is eliminated.
b) Mycolic acid esterification: 2 mL of methanol: toluene: sulphuric acid (30:15:1; vol/vol) is added on each tube, and esterification is achieved overnight. Then, 4 mL of n-hexane is added. It is dried under nitrogen flow and it is resuspended with 500 μl hexane.
c) TLC: 10 μl of each sample is applied on a line parallel to the edge of the plate (Silica gel 60 (20×20 cm) (Merck). The chromatographic separation is performed in a saturated tank with a mobile phase (ethylic ether: n-hexane (15:85, vol/vol)) by three times. Then, the plate is allowed to dry in air.
d) Mycolic acids are revealed by spraying the plates with a solution of phosphomolybdic acid in 96° ethanol and heat at 120° C. for 10 min.

Mycolic acids in FCMtb samples are determined by comparison with mycolic acid commercial standard spot. Results are expressed as qualitative data (presence (positive)/absence (negative) of mycolic acid assessed.

f) Identification of Trehalose 6,6'-Dimycolate (TDM):

Test samples: Lyophilised FCMtb, 40 mg. Reference solutions: TDM standard (Sigma). Procedures (i) Extraction process: The sample is extracted with chloroform:methanol (1:1; vol/vol) and then it is incubated overnight. The supernatant fraction is dried under nitrogen flow and it is weighted. Finally, dried samples are resuspended in chloroform at 40 mg/mL final concentration.

(ii) TLC: 10 μl of each sample is applied on a line parallel to the edge of the plate (Silica gel 60 (20×20 cm) (Merck). The chromatographic separation is performed in a saturated tank with a mobile phase (chloroform: methanol: water (60:12:1; vol/vol). Then, the plate is allowed to dry in air.

(iii) Detection: The TDM is revealed by spraying the plates with a solution of antrone 1% in sulphuric acid and heat at 120° C. for 5 minutes.

(iv) Identification: TDM in FCMtb samples is determined by comparison with commercial TDM which is used to generate a standard spot. Results are expressed as qualitative data, i.e. presence (positive)/absence (negative) of TDM assessed.

g) Identification of Lipoarabinomannan (LAM):

For Western Blot analysis of LAM, compounds are separated by SDS PAGE according to standard methods and then electrophoretically transferred onto a nitrocellulose membrane for immunodetection using specific antibody CS35. The interaction antigen-antibody is visualized by incubation with an anti-antibody (IgG Goat anti-mouse IR Dye 800 CW) which triggers a fluorescent reaction.

h) Sterility

All processes which require sterility, according to the knowledge of the person skilled in the art, are carried out under sterile conditions; this also applies if sterility is not explicitly mentioned for any given step which requires the same. Sterility test is assessed as prescribed in Ph. Eur. 2.6.1 (USP <71>).

i) Mycobacteria Inactivation

The inactivation of mycobacteria is assessed in accordance with Ph. Eur. 2.6.2 j) Bacterial Endotoxins

The test for bacterial endotoxins (LAL test, Limulus Amoebocyte Lysate) is performed according to the general indications of the Ph. Eur., method 2.6.14, following Method D (Chromogenic kinetic method) as well as USP <85>.

Fragmentation of the Bacilli

The choice of fragmentation of the bacilli is thought to allow optimal presentation of cell antigens, particularly cell wall antigens. Fragmentation of the FCMtb is determined by both Dynamic Light Scattering (as described below) and Laser diffraction methodologies.

Laser diffraction allows measuring the fragmentation in a range between 0.04 μm and 2000 μm. The assay is carried out in the Servicios Cientifico-Técnicos de la Universitat de Barcelona, Spain. Instrument: Coulter LS 13320 equipped with a Universal Liquide Module (ULM). Solvent: purified water/mineral oil. Results: plotted as a histogram, expressing the relative frequency of the number of particles (%) in front of the particle diameter (0.04 μm-2000 μm).

Determination of z-Average Particle Size and Polydispersity Index

The average particle size as described in this document is determined by dynamic light scattering (DLS), which is based on the physical concept of the Brownian motion of particles, defined in the Stokes-Einstein equation:

$$d(H) = \frac{kT}{3\pi\eta D}$$

wherein:—

D(E)=hydrodynamic diameter

D=translational diffusion coefficient k=Boltzmann's constant

T=absolute temperature

η=viscosity

Without wishing to be limited to any particular theory, the Stokes-Einstein equation establishes that particles suspended in a liquid medium are in a constant and random movement, with a speed that depends on their size: the larger the particle is, the slower the Brownian motion will be.

In dynamic light scattering measurements, the sample containing the particles to be measured is illuminated with a monochromatic light source, preferably a laser, and analyzed in a correlation function how the intensity of scattered light fluctuates with time. If, for instance, large particles are being measured, as they move slowly, the intensity of scattered light fluctuates slowly, and the correlation takes long time to decay; on the other hand, if small particles are being measured, as they move quickly, the intensity of scattered light fluctuates quickly, and the correlation of signal decays more rapidly.

According to this invention, the particles are preferably measured with the following instrument: Zetasizer nano zs (Malvern Instruments), using purified water/mineral oil as solvents.

If nothing to the contrary is indicated, the instrument is used according to the manufacturer's instructions, and adjustment and calibration, if applicable, are also according to the manufacturer's instructions.

The size is calculated from the correlation function using various algorithms. In the present case, the 'cumulants analysis', as defined in ISO13321 Part 8 is applied. The correlation function fits results in a single exponential curve that allows for calculation of the following parameters:

The mean size, or z-average diameter, of the particle distribution. This mean size is the intensity mean.

The polydispersity index (pdi), i.e. corresponding to the width of the particle size distribution.

The results are typically plotted as a histogram, expressing the relative frequency of the number of particles (%) with respect to the particle diameter which may be any diameter which is comprised in the range from 1 nm to 3 μm.

Induction of Asthma in Mice and Administration of Compounds

In order to sensitize the mice, female BALB/c mice (8 weeks old at the beginning of the experiment) were injected i.p. 20 μg of OVA (grade V)+2 mg Alum on days 0 and 14 of the study. During the challenge phase all animals (including non-sensitized) were exposed (days 28-30) by nebulisation to a solution of 1% OVA. One group of OVA-sensitized mice was administered FORMULATION A as a preventive measure/Formulation A P (p stands for preventive), and another as a therapeutic agent (Formulation A T (T stands for therapeutic), both receiving 200 μg/dose. As a positive control the inventors utilized sensitized mice treated with Pfizer's BCG Danish Strain 1331, subcutaneously with 150 μg/dose on day −31. As a negative control sensitized mice were administered a placebo (the vehicle of the FORMULATION A vaccine). Also included were two non-sensitized groups, each treated with either the control vaccine (BCG) or the test vaccine (FORMULATION A), thus establishing the following 7 conditions/experimental groups:

Group 1 (control): non-sensitized mice treated with the vehicle (n=8)

Group 2 (control −): sensitized mice treated with the vehicle (n=8)

Group 3 (control BCG): non-sensitized mice treated with the BCG vaccine on day −31 (n=8)

Group 4 (control +): sensitized mice treated with the BCG vaccine on day −31 (n=8)

Group 5 (control FORMULATION A®): non-sensitized mice treated with FORMULATION A (Preventive) (n=8)

Group 6 (test): sensitized mice treated with FORMULATION A (Preventive) (n=8)

Group 7 (test): sensitized mice treated with FORMULATION A (Therapeutic) (n=8)

Figure 10:
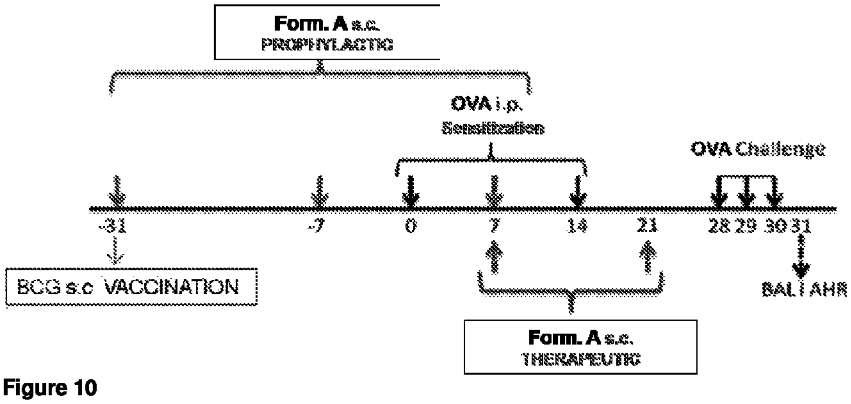
FIG. 10 shows a schematic summary of the protocol: induction of asthma, treatment with FORMULATION A (see Example 11), those variables that were measured both in treated animals and in controls.

The vaccines and placebo were supplied by the inventors in individual vials. These vials were reconstituted just prior to daily administration in a laminar flow hood. All vaccine doses and placebos were administered subcutaneously in the back at the time-points shown in FIG. 10.

Sampling and Airway Parameters Assessments

Due to the large number of animals involved, the experiment was carried out in 4 rounds, each temporarily overlapping with that before it, and each performed identically in accordance with the protocols for asthma induction and treatment. Animals were monitored throughout the entire experiment and samples were taken for later analysis.

Monitoring of Mice

The inventors recorded the weight of all mice from the first day of administration (−31) and continuing weekly until the day of sacrifice. Mice under each treatment regimen were carefully assessed using a standardized protocol that included behavioural monitoring and observation of hair and mucous membranes.

Determination of Lung Functionality

The degree of reactivity was measured in 8 mice from each group. The inventors examined airway reactivity in all mice 24 hours after the last challenge with OVA (day 31) by assessing the degree of bronchial reactivity to methacholine via invasive plethysmography (Fine Pointe, Buxco Europe Ltd, UK). Lung resistance was determined in tracheotomised animals (following sedation and anaesthesia) as a measurement of airway response to bronchoconstrictor stimuli.

Assessment of inflammation—bronchoalveolar lavage (BAL)

After evaluating lung functionality, all still-anesthetized animals were sacrificed by exsanguination. This was followed by a bronchoalveolar lavage (BAL) in order to harvest cells and molecules from the tracheobronchial tree. BAL was performed by repeated endotracheal injection with 0.3 ml of PBS+2% FCS. An aliquot was taken from the aspirated fluid and total cells were counted in order to assess the degree of inflammation. The remaining BAL fluid was centrifuged, cells being placed into a cytospin to carry out a differential count using Diff-Quick staining, and the supernatants being stored for later analysis.

Sampling

In addition, lung and serum samples were collected and stored at −80° C. for later identification of proteins of interest by ELISA. At the same time, blood samples were refrigerated overnight and serum was aliquoted and stored at −20° C.

EXAMPLES

The invention is in the following illustrated by examples. The examples are for illustrative purposes and should by no means be understood as limiting the scope of the present invention.

Example 1: Isolation of the Strain *Mycobacterium tuberculosis* NCTC 13536

The starting material for the production of FCMtb is an inoculum of the strain NCTC 13536, synonymously called 511 or *Mycobacterium tuberculosis* NCTC 13536, a strain of *Mycobacterium tuberculosis* isolated from an immunocompetent patient diagnosed with pulmonary tuberculosis in Barcelona, Spain. It was deposited in 2010 at the NCTC in London, which is an official depositary organisation according to the Budapest Treaty. The strain has additionally been deposited by the strain collection of the Service of Microbiology of the Hospital de Sant Pau, Barcelona, Spain.

Two passages of the original strain have been performed in the years 1995, and 1996 respectively. MSL PB#1 corresponds to the second passage of the original strain of *M. tuberculosis* NCTC 13536, which was performed in October 1996 resulting in 100 vials (3 ml sterile glass vials) stored at −70±5° C. The strain has a low genetic polymorphism, as identified by standard methods in the art.

Example 2: Upstream Process for Production of MTB-C Cells

Figure 1:
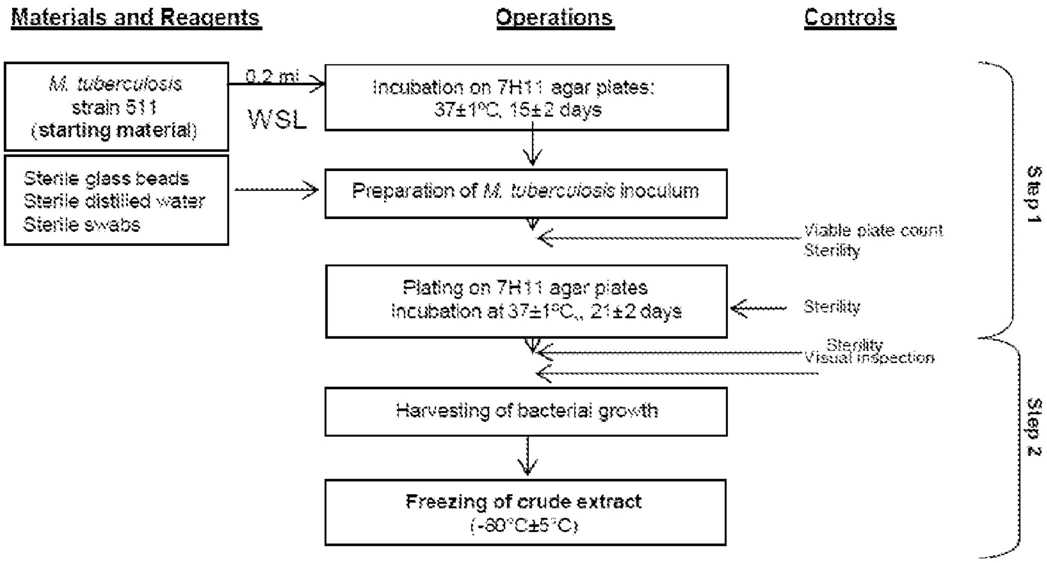
FIG. 1: Flow-chart showing upstream process of the drug substance FCMtb, including the materials and reagents involved in the process and suitable in-process controls.

A flow-chart of this process is given in FIG. 1. The starting material for the production of FCMtb is an inocculum of the strain *Mycobacterium tuberculosis* NCTC 13536 (Example 1). In order to ensure the continued supply of this starting material, a seed lot system is preferably used. Hence, a working seed lot (WSL) derived from a master seed lot (MSL) is used for production of FCMtb. *Mycobacterium tuberculosis* NCTC 13536 (Example 1) is cultured for 3-5 weeks in Löwenstein-Jensen medium. The bacterial growth is then sub-cultured in Proskauer Beck media at 37±2° C. with stirring at 100±5 rpm. Once the maximum bacterial concentration (by visual inspection) is achieved, a subculture in Proskauer Beck media is started and incubated. When a similar bacterial concentration is achieved, small aliquots are taken. The viable bacterial count is determined by the number of colony forming units (CFUs) obtained in Middlebrook agar medium after incubation at 37±2° C. for 3-4 weeks. The bacterial count must be 2-5×$10^7$ CFUs/ml.

(1) Culture of *Mycobacterium tuberculosis*

The production of FCMtb begins with the seeding of 0.2 ml of a WSL in a 7H11 agar plate and incubation at 37±1° C. for 15±2 days. Then, colonies are transferred into a tube containing a few glass beads. After mixing, approximately 5 ml of water for injection (WFI) is added to obtain a bacterial suspension. At this point, a viable plate count and a sterility test are performed. About 100 Middlebrook 7H11 agar plates are seeded with *M. tuberculosis* using swabs soaked with the bacterial suspension to obtain confluent cultures. The plates are incubated at 37±1° C. for 21±2 days.

Sterility Test as in-Process Control is Performed as Follows:

The sterility testing is aimed to ensure the absence of fungi and bacteria other than Mycobacteria. The tests are carried out by direct inoculation, following the conditions described in Ph. Eur 2.6.1 for the sterility test. Samples tested must be sterile. Medium 7H11 is used instead of 7H10 (as is mentioned in Ph. Eur. 2.6.2). 7H11 is based on medium 7H10 adding one gram of pancreatic digest of casein in order to enhance the growth of strains of *Mycobacterium tuberculosis*.

(2) Harvest of *Mycobacterium tuberculosis* and Freezing of Crude Extract

After the incubation period, the purity of the bacterial culture is controlled by a visual inspection of the agar plates and the performance of a sterility test. Then, bacterial growth is collected from agar plates and transferred into a sterile tube. The crude extract obtained is weighed (20-22 g). The mixture is kept at −80° C.±5° C.

Figure 2:
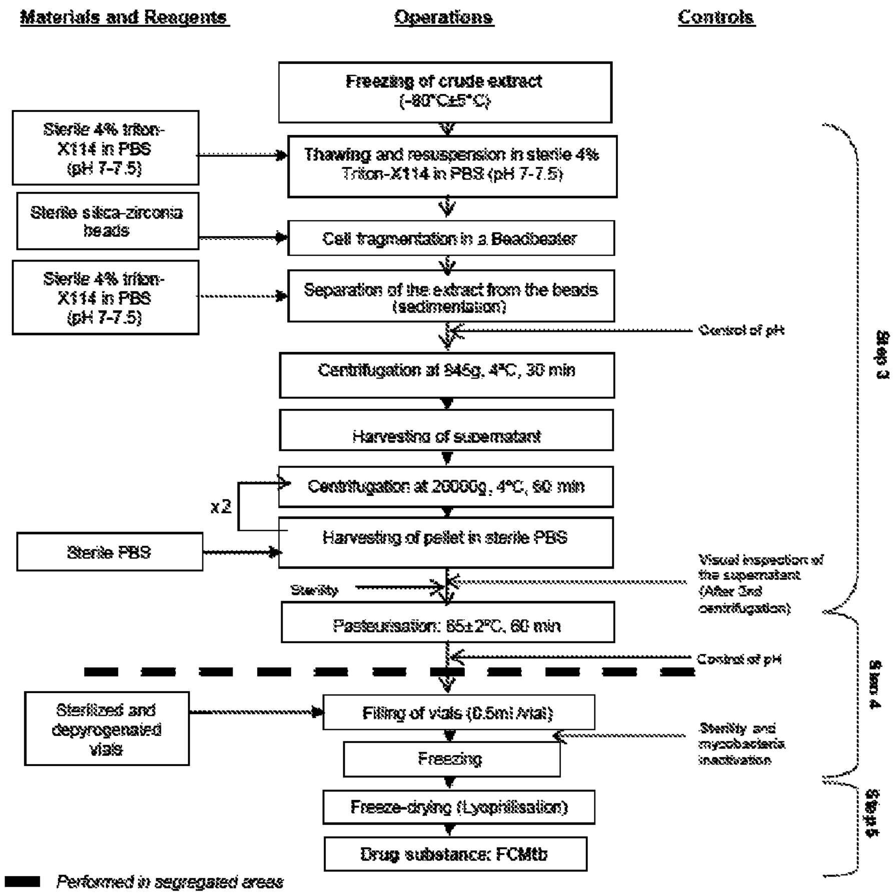
FIG. 2: Flow-chart showing downstream process of the drug substance FCMtb, including the materials and reagents involved in the process and suitable in-process controls.

Example 3: Downstream Process for Production of Liposomes Obtained from the Crude Extract A flow-chart of this process is given in FIG. 2.

(3) Cell Fragmentation and De-Lipidation

The frozen crude extract (Example 2) is thawed at 37±1° C. and sterile PBS buffer with 4% (w/w) Triton-X114 (pH 7.0-7.5) is then added at 4° C. After mixing, it is subsequently transferred into a sterile polycarbonate container containing sterile silica/zirconia beads. Then, cell fragmentation is carried out in a Beadbeater by applying the following fragmentation method: 3 cycles, each one consisting of 5 periods ON/OFF plus 10 minutes of break. Once the process is finished, the cellular fragmented fraction is separated from the beads by subsequent washings (repeated shaking and sedimentation) in sterile PBS buffer with 4% triton-X114, (pH 7-7.5). An aliquot of the washed suspension of the cellular fragmented fraction is then collected for pH control and a final centrifugation at 845 g at 4° C. for 30 minutes proceeds.

To remove the cytosolic fraction and to obtain a suspension enriched in cellular fragments, a high speed centrifugation is performed twice at 20000 g approx. for 60 minutes, at 4° C. After the first centrifugation, the yellowish supernatant (rich in soluble proteins and lipids) is discarded and the pellet is resuspended in PBS and further centrifuged under the same above described conditions. After that, the appearance of the discarded supernatant must be clear and colourless. Finally, the obtained pellet is resuspended in a final volume of 50-60 ml PBS (FCMtb suspension)

(4) Pasteurization

The FCMtb suspension is then pasteurized at 65±2° C. for 60 min. Once pasteurization is finished pH of the pasteurized FCMtb is determined by litmus paper. It is considered acceptable in the range pH 6.5-7.5. Sterile and depyrogenated vials are filled with 0.5 ml of the product suspension and IPCs on Sterility and Mycobacteria inactivation are performed. Finally, filled vials are frozen at −80±5° C. Once the material is subjected to pasteurisation, it will be physically segregated from untreated material, i.e. the spaces used before pasteurisations are clearly separated from those used during the subsequent filling process.

(5) Freeze-Drying

All vials containing the product frozen are then lyophilised at about −45° C. to 30° C. temperature and at 0.310 mbar pressure for approximately 18 hours (0.5 ml volume per vial). Using aseptic techniques and under $N_2$ atmosphere, the vials are stoppered and labelled. The packaged drug substance is then stored at −20°±5° C. for up to 12 months.

Example 4: Protein Characterization

Figure 3:
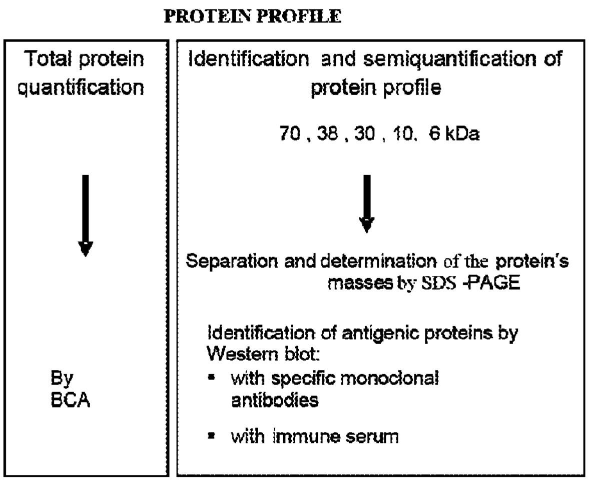
FIG. 3: Flow-chart of protein characterization.

FIG. 3 gives an overview of the characterisation strategy in terms of protein profile.

Based on literature (Andersen P., 1997, Scand J. Immunol.; 45(2):115-31; Geisel et al., 2005, J. Immunol.; 174(8): 5007-15; Stewart et al. 2005, Infect. Immun., 73(10):6831-7., Wang et al., 2007, J. Mol. Biol., 366(2):375-81), 6 protein bands were selected as being representative for protein profile assessment: HSP70 protein (Rv0350), 38 kDa protein (Rv 0934), (Rv 1866c), 19 kDa protein (Rv 3763), CFP10 protein (Rv3874), and ESAT-6 protein (Rv3875).

A. Determination of total protein content: Total protein levels in FCMtb are quantified by bicinchoninic acid (BCA) methodology. Total protein represents about 10% (w/w) of FCMtb content. Reference standards FCMtb-0429-16 and FCMtb-52.1 contain 167 μg protein/mg FCMtb and 115 μg protein/mg FCMtb, respectively.

Figure 4:
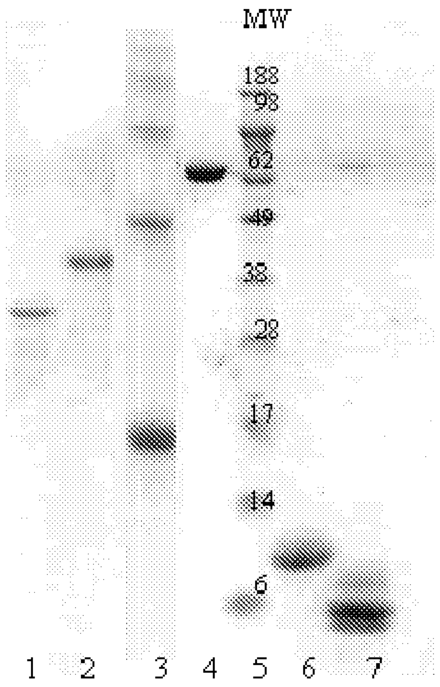
FIG. 4: Identification of antigens by SDS-PAGE and Coomassie Blue Stain methodology. Reference antigens ESAT6 (6 kDa) (7); CFP10 (10 kDa) (6); Ag85B (30 kDa) (1); 38 kDa (2); HSP70 (70 kDa) (4) as well as Molecular Weight marker MW (5), are shown.

B. Identification of protein profile by sodium dodecyl sulphate polyacrylamide gel electrophoresis (SDS-PAGE): The protein profile of the drug substance FCMtb was determined by comparison with reference antigens from *Mycobacterium tuberculosis* corresponding to ESAT6 (6 kDa) (7); CFP10 (10 kDa) (6); Ag85B (30 kDa) (1); 38 kDa (2); HSP70 (70 kDa) (4) as well as Molecular Weight marker MW (5), are shown (see FIG. 4). Determination of protein profile of drug substance FCMtb and identification of bands (approximately 70 kDa, 38 kDa, 30 kDa, 10 kDa and 6 kDa) is carried out by Coomassie staining. Identification of the 19 kDa band (lipopolypeptide) is carried out by silver staining.

Figure 5A:
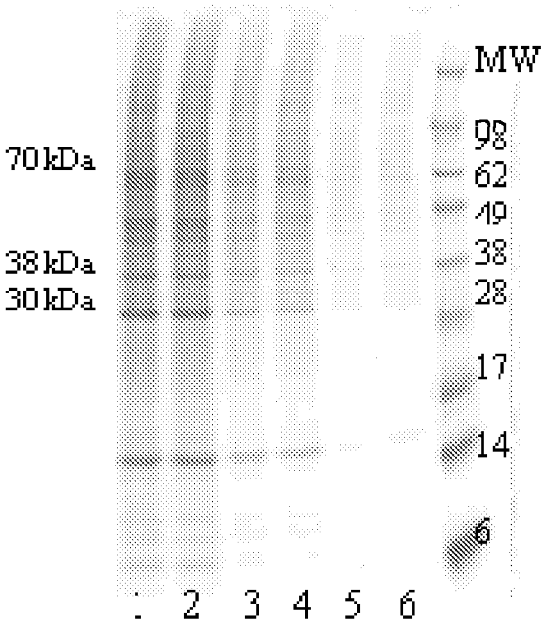
FIG. 5*a*: Protein profile: Protein profile of reference standard FCMtb-52.1 (1 to 6) at final concentrations of 15.6 μg FCMtb/mL (1, 2), 6.25 μg FCMtb/mL (3, 4) and 1.56 μg FCMtb/mL (5, 6), SDS page followed by Coomassie stain. MW in kDa. 5b: Identification of the 19 kDa band, SDS page followed by silver staining. 5c: Protein profile: Identification of bands (10 kDa and 6 kDa) in the indicated FCMtb batches by SDS-PAGE and Silver Stain methodology carried out in parallel with ESAT-6 standard from Lionex. Different FCMtb batches (1, 2, 3, 9, 10, 11, (batch FCMtb-52.1 in lane 9)), ESAT-6 standard from Lionex at different concentrations (4 to 8); 5d: Western Blot Identification of antigen *M. tuberculosis* HSP70 (Rv0350) in FCMtb batches by Western-blot using specific antibodies parallel to *M. tuberculosis* HSP70 standard. Different FCMtb batches (1, 2, 3, 4, 7, 8, 9), HSP70 standard (5,6); 5e: Identification of antigen *M. tuberculosis* 38 kDa (Rv 0934) in FCMtb batches by Western-blot methodology using a specific antibody and carried out in parallel with *M. tuberculosis* 38 kDa standard from Lionex. Fluorescence detection using the Odyssey System. Different FCMtb batches (1, 2, 3, 6, 7), 38 kDa standard (4, 5). 5f: Identification of antigen Ag85B (Rv 1886c) in FCMtb batches by Western-blot methodology using a specific antibody and carried in parallel with *M. tuberculosis* Ag85B standard from Lionex. Fluorescence detection using the Odyssey System. FCMtb batches (1, 2, 3, 5, 6, 7), Ag85B standard (4).
Figure 5B:
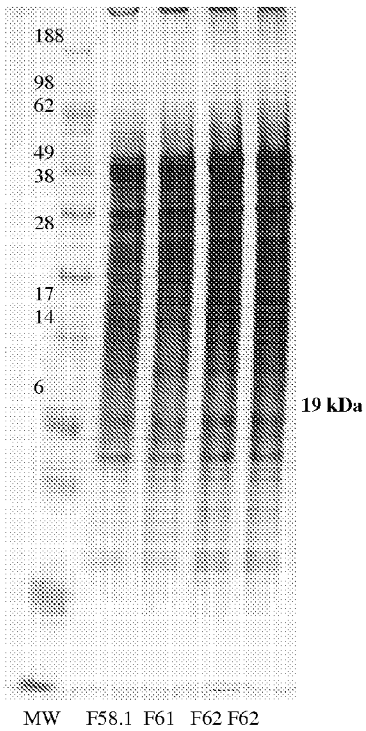
FIG. 5: Protein characterisation.
Figure 5C:
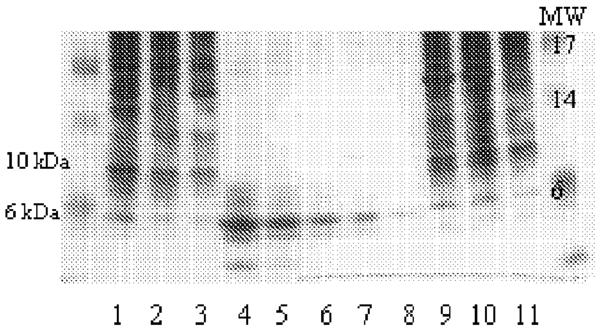
Figure 5D:
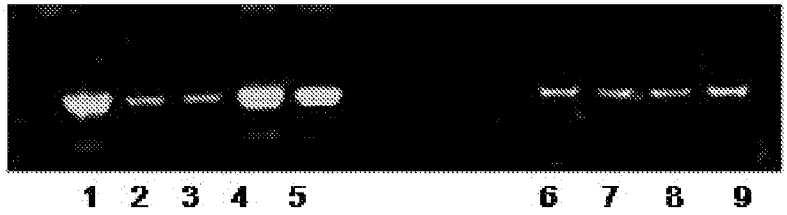
Figure 5E:
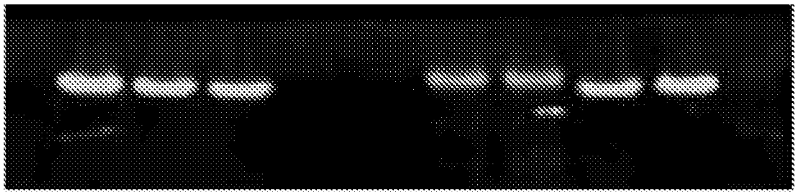
Figure 5F:
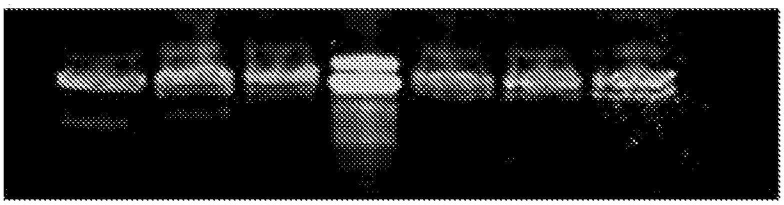
Figure 6:
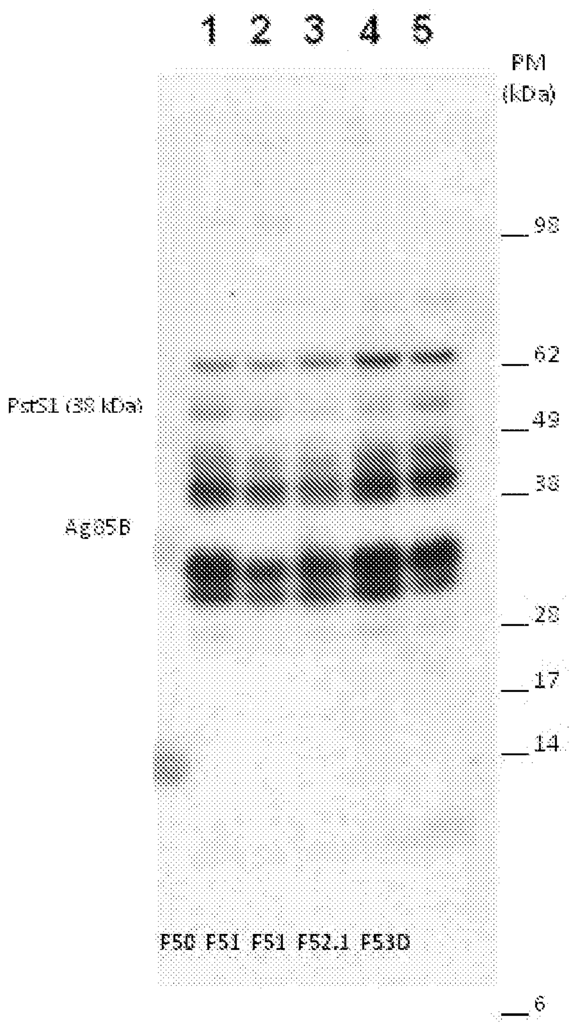
FIG. 6: Interaction of indicated protein bands of different FCMtb batches (50 μg/lane) with 1/8000 diluted serum obtained from infected mice after being inoculated twice with the liposome formulation based on pharmaceutical vaccine composition according to this invention, using Western-blot methodology.

C. Identification of the protein profile by Western-blot with specific monoclonal antibodies: The protein profile of the drug substance FCMtb is determined by the patterns obtained using Western-blot analyses with monoclonal antibodies (mAb): Anti-HSP70 (70 kDa, FIG. 5*c*), anti-38 kDa (FIG. 5*d*), anti-Ag85B (30 kDa, FIG. 5*e*).

FCMtb-52.1 is the reference batch for FCMtb according to the preferred mode of carrying out this invention.

Example 6: Lipid Characterisation

Figure 7A:
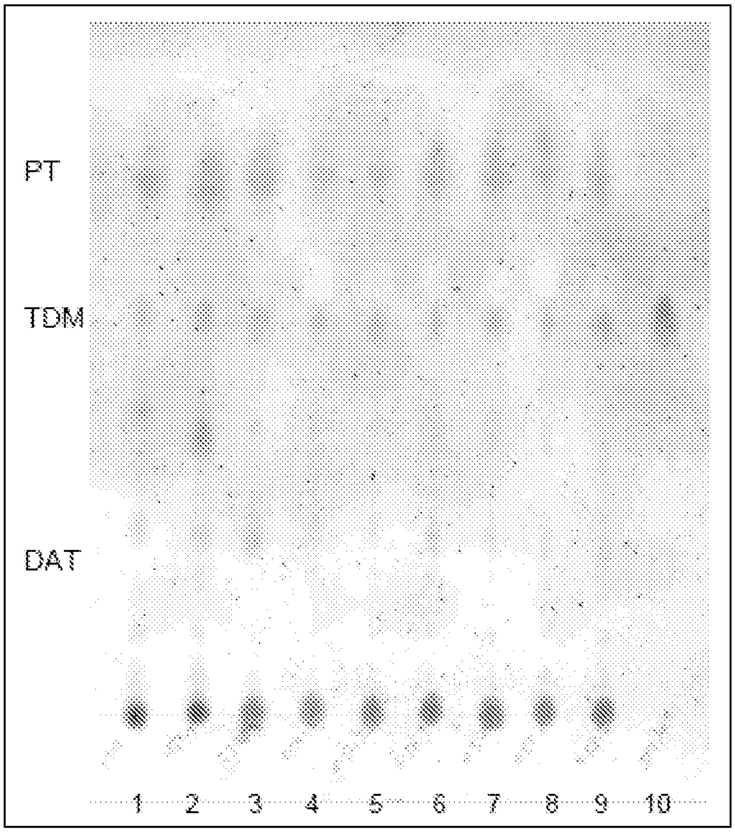
FIG. 7: Lipid analysis. 7a: Identification of polyacyltrehalose (PT), trehalose 6,6'-dimycolate (TDM) and diacyltrehalose (DAT) in reference strains (H37Rv (2) and NCTC 13536 (1) and different FCMtb batches (3-9), and TDM standard (10) by TLC methodology. 7b: Identification of trehalose 6,6'-dimycolate (TDM) in FCMtb batches by TLC methodology. Panels (A) and (B) represent two independent assays. (A) TDM standard (11) and (12), other lanes different FCMtb batches. B: (1) TDM standard (1), other lanes different FCMtb batches. 7c: Pattern of mycolic acids I, III and IV in FCMtb batches by TLC methodology. Panels (A), (B) and (C) represent three independent assays. (A) FCMtb batches (1-6 (FCMtb-51.2 standard 6)). (B) for illustration/reference, (C) batch FCMtb-47b (1) compared with mycolic acid standard (2). 7d: Identification of LAM (reference in left lane, samples derived from liposomes according to the invention in remaining lanes).
Figure 7B:
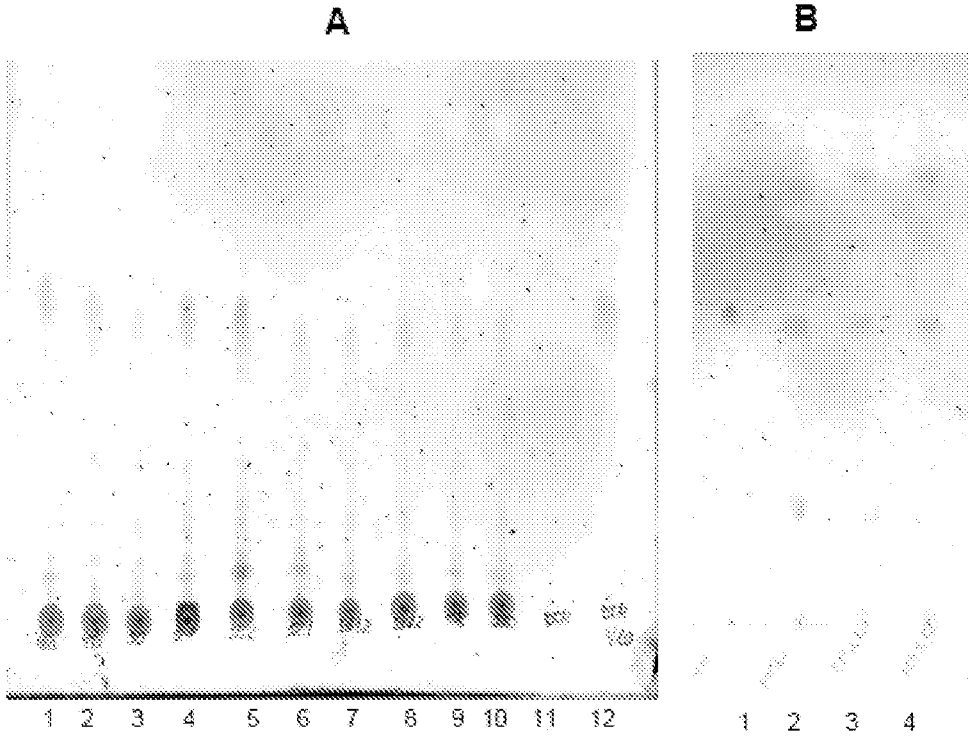
Figure 7C:
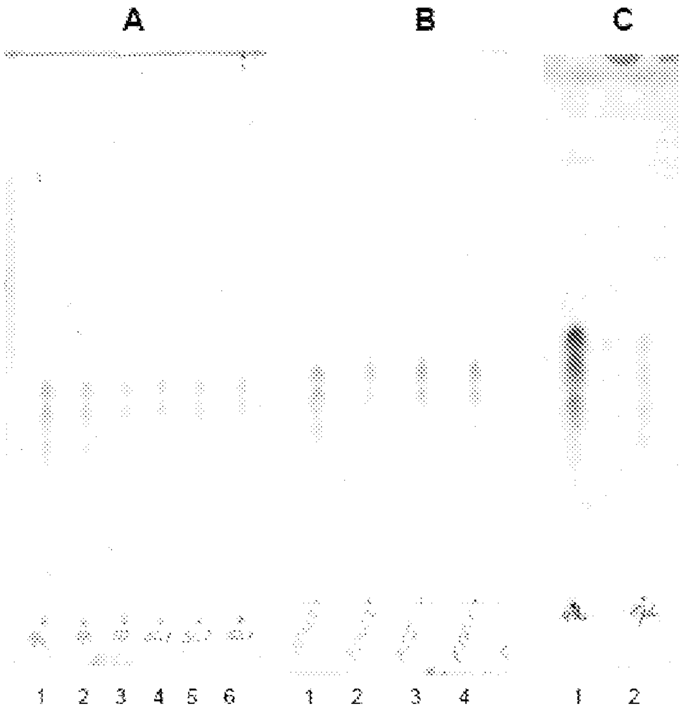
Figure 7D:
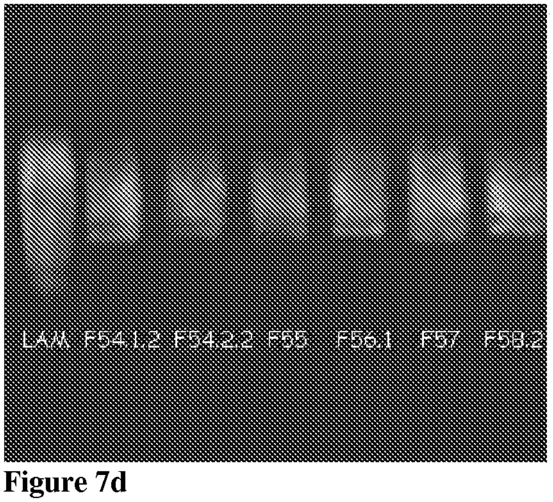

The characterisation of the lipid profile of FCMtb consists of a fractionating process based on chloroform:methanol (1:1) extraction. The fractionating process carried out in these studies has been based on the procedure described by Delmas et al., 1997, Glycobiology 7(6), 811-7. Thin layer chromatography (TLC) has been the method used to analyse the content of lipids and glycolipids present in FCMtb. Specifically, polyaciltrehalose (PT), trehalose dimycolate (TDM), diacyltrehalose (DAT), phosphatidilinositolmannosids (PIMs) and other phospholipids, as well as phthiocerol dimycocerosates (PDIM) and Mycolic acids have been identified by thin layer chromatography (TLC) both in the reference strains H37rv and NCTC 13536, as well as in different FCMtb batches. See FIG. 7*a*. The content of trehalose 6,6'-dimycolate (TDM) is analysed by TLC in the supernatant. Mycolic acids determination is conducted in the sediment, following a TLC method. Although no quantitative data are known for the lipid profile of MTB-C, the qualitative lipid profile established in the studies is in line with current scientific knowledge and allows for a standard characterisation of the immunogenic lipids so far known. FCMtb have been compared with whole cell lipid fraction of strains NCTC 13536 and H37Rv of *M. tuberculosis* and TDM commercial standard (see FIGS. 7*a* and 7*b*). Overall, the lipid content has been shown to be consistent in different batches of FCMtb-comprising liposomes according to this invention. FIG. 7*d* shows the identification of LAM.

Example 7: Characterization of Fragmented Cell Material

Preliminary results using both methodologies show that the fragments size of FCMtb is mainly below 1 μm (99%<1 μm) which is corroborated by FCMtb electronic microscopy: the fragment size ranges mainly from 100 to 300 nm.

Levels of residual DNA after extraction with a phenol/chloroform mixture have been investigated by absorbance at 260 nm (detection limit: 0.2 μg DNA/mg FCMtb). Typical results obtained so far are below 15 μg DNA/mg FCMtb.

The consistency of the production process of the drug substance is shown by a lipid and protein profile that is reproducible for different FCMtb batches.

Example 8: Effect of Sucrose

In an initial test, one of the following excipients (a) 1.5% glycine and (b) 5% sucrose, respectively, was optionally incorporated into a liposome formulation comprising fragments of the MTB-C strain NCTC 13536. Subsequently, a comparative evaluation is undertaken on physicochemical properties and biological activity associated to both formulations.

Results obtained by measurement after reconstitution of the lyophilized liposome composition and after testing according to the current batch release specification parameters are presented in Table 5.

TABLE 5

Results of specifications for 3 different formulations, measured after reconstitution of the lyophilized liposome composition.

| | | | | FCMtb formulated in a liposome suspension | | |
|---|---|---|---|---|---|---|
| Parameter | | Acceptance criteria | | Without excipient | Sucrose 5% | Glycine 1.5% |
| | | | | FCMtb formulated in a liposomal suspension | | |
| Appearance | | White to off-white powder | | ND | Complies | Complies |
| Cake morphology | | Flat to almost flat and homogeneous | | ND | Complies | Complies |
| Water content (%) | | ≤3% | | ND | 1.4 | 3.0 |
| Time to reconstitution (s) | | Well reconstituted ≤10s | | ND | 5 | 12 |
| pH | | 7-8 | | 8.1 | 7.4 | 7.0 |
| Particle size | z-average (nm) Pdi [a] | 75 ± 20 (≤0.250) | | 370 [1] (0.492) | 66 (0.215) | 504 [1] (0.569) |
| Immunogenic potency in *M. Tuberculosis* infected murine model | Antigen-specific IFN-γ Spot forming units | PPD | 3-12 Ratio SFU/$10^6$ cells with respect to basal value (Basal value in SFU/$10^6$ cells) | 3.6 (183) | 5.1 (183) | 2.8 (183) |
| | | Ag85B (30 kDa) | 5-20 Ratio SFU/$10^6$ cells with respect to basal value (Basal value in SFU/$10^6$ cells) | 5.5 (73) | 9.6 (73) | 5.4 (73) |

[a] Polydispersity index

[1] Presence of liposomal aggregates

ND = not determined

Figure 8:
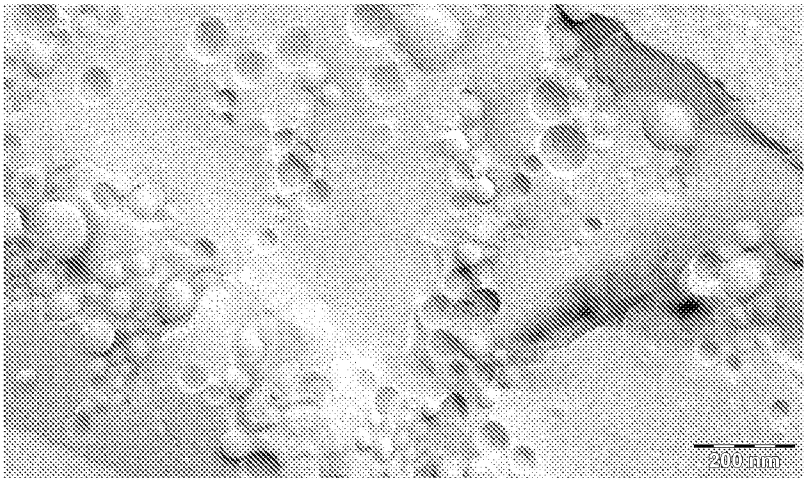
FIG. 8: Freeze-fracturing preparation of liposomal concentrate (LCS) bulk (electronic microscopy).

The investigators of this study surprisingly found that 5% sucrose formulation provides the advantage of better physicochemical results, such as water content or time to reconstitution, respectively. But the most crucial fact is the important reduction in liposomal aggregation (particle size, z-average) shown with the sucrose-comprising formulation in comparison with the other two formulations. Analysis by Dynamic Light Scattering has shown a z-average of 75±20 nm (polydispersity index 0.350) of the sucrose-containing liposomes. Electron microscopy of freeze-fracturing preparations of the sucrose-containing liposome formulation shows a mixture of multilamellar and unilamellar liposomes with sizes between 40 and 100 nm (FIG. 8).

Due to this improved parameter together with the observed lesser water content levels (2%) for the 5% sucrose formulation, improved stability results are expected for this formulation. This is indeed the case.

Example 9: Manufacturing Process of the Lyophilized Liposome Formulation (Formulation A)

Figure 9:
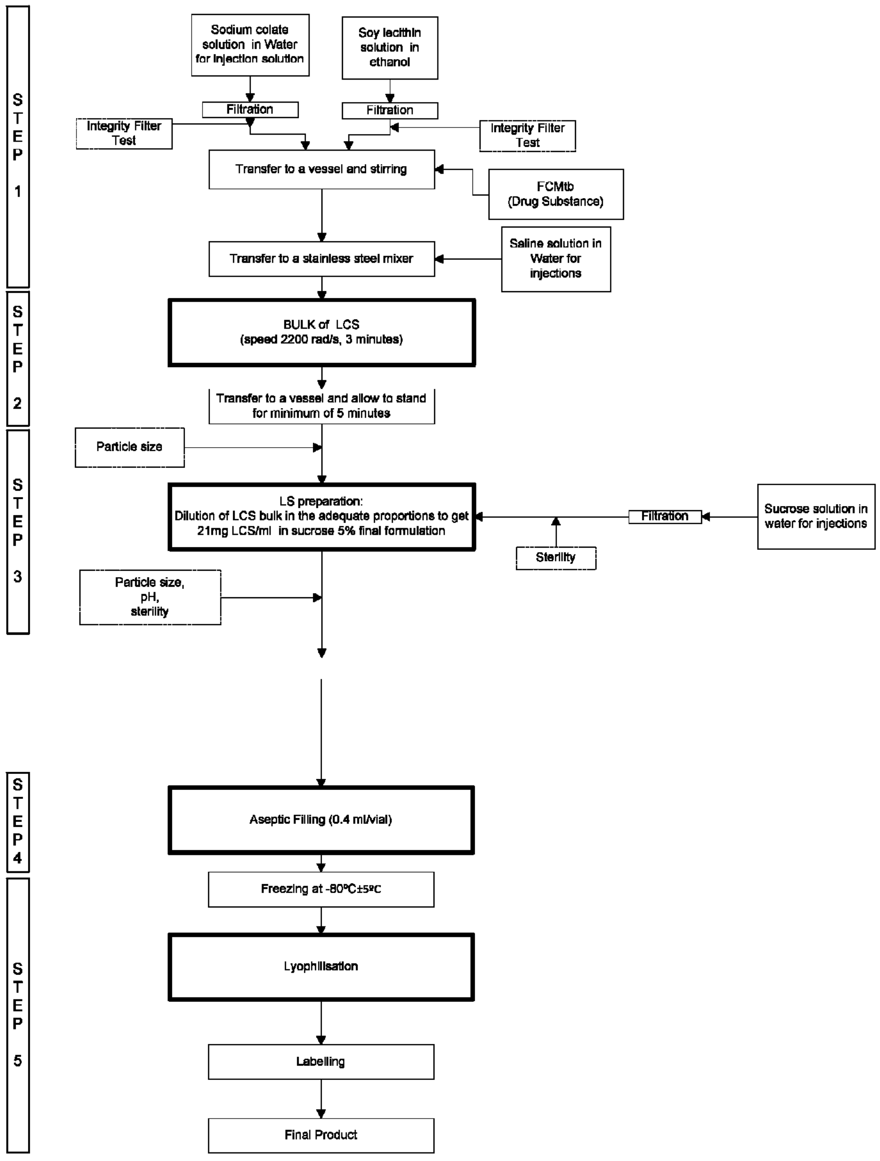
FIG. 9: Flow-chart of the process according to the preferred mode of carrying out this invention.
Figure 11:
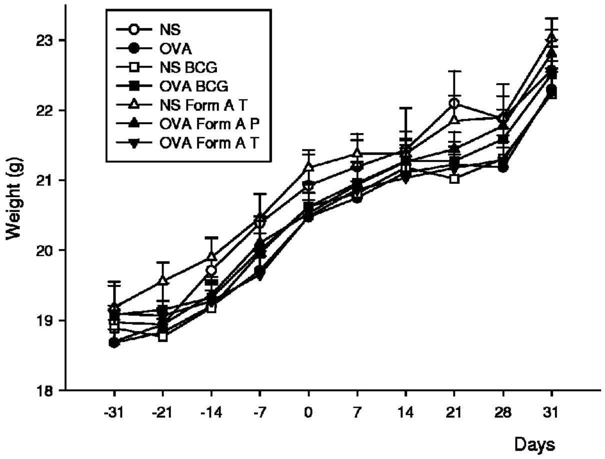
FIG. 11: Representation of the results in a bar-chart graph displaying the average of all individual values.
Figure 12:
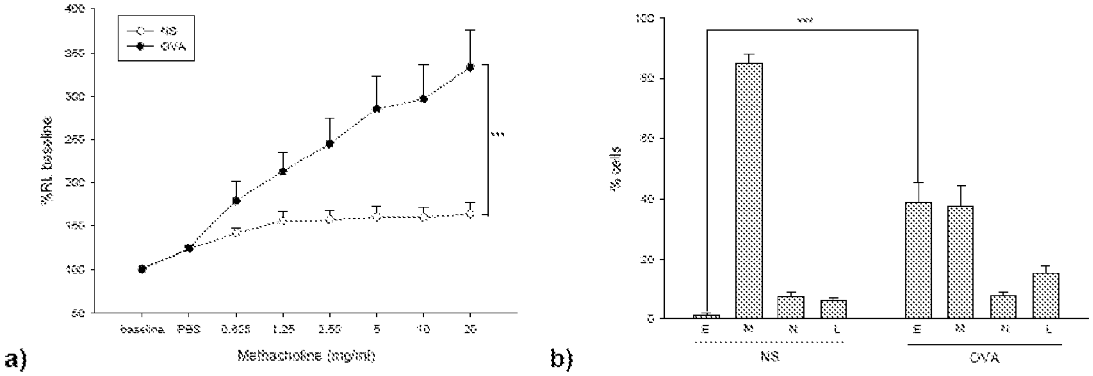
FIG. 12 shows the effects that exposure to OVA had on the untreated animals, comparing lung function and eosinophil recruitment in sensitized versus non-sensitized animals. As the data indicates, the sensitization process was efficient since those animals exposed to OVA exhibited a clear and significant ($p<0.001$, ANOVA 2-factor) increased airway response to methacholine when compared with non-sensitized animals (FIG. 12*a*). In addition, the airways of non-sensitized animals contained very low numbers of eosinophils, while in the airways of those sensitized to OVA the inventors detected a significant increase ($p<0.001$, t test) of pulmonary eosinophilia (FIG. 12*b*). The present model thus facilitates an assessment of the potential effects stemming from the tested treatments.
Figure 13:
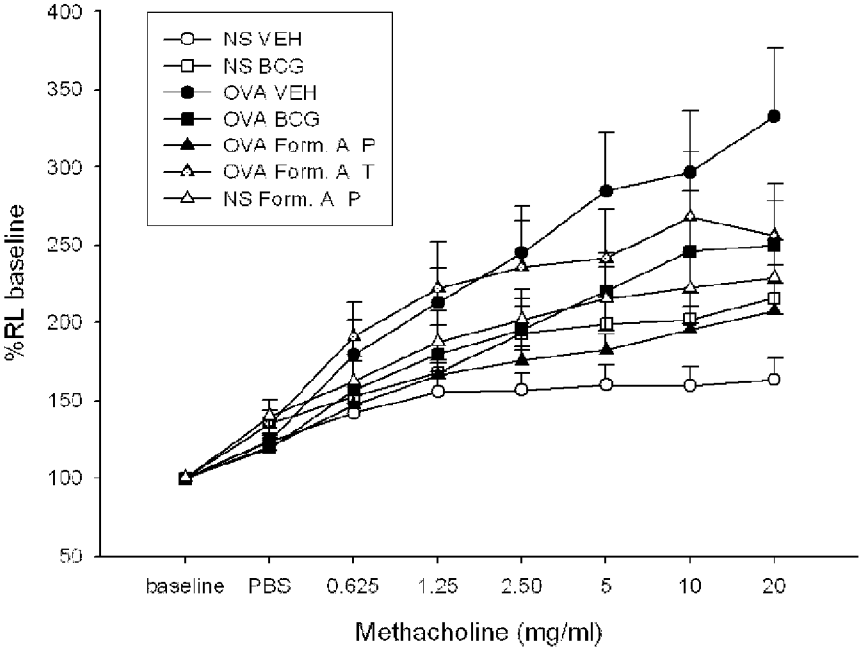
FIG. 13 shows bronchial reactivity in response to increasing doses of methacholine in 7 groups of mice, while FIG. 14 displays the four different treatment groups (a, b, c and d). In order to simplify the overall data representation, statistical significance is indicated only in FIG. 14.

One embodiment of the manufacturing process of a pharmaceutical composition comprising the liposome formulation according to the present invention is shown in FIGS. 9 and 11. Briefly, it comprises the following steps 1 to 5.

(1) Preparation of the LCS Bulk Components

LCS bulk soy lecithin is dissolved in ethanol (1:1; w/w) and sodium cholate is dissolved in water (1:5; w/w). The solutions are sterilized by filtration. After mixing of sodium lecithin solution and sodium cholate solution, lyophilised FCMtb (Example 1) is added upon stirring. The ratios of the components are 0.03:0.2:0.7 (FCMtb:sodium cholate:soy lecithin; w/w/w).

(2) LCS Bulk Preparation

The aqueous phase of is transferred to a sterilised stainless steel mixer. The lipid phase of (1), containing soy lecithin, sodium cholate, and FCMtb, is added in a ratio 0.7:0.3 (aqueous phase:lipid phase, w/w). The phases are mixed at 2200 rads/s for 3 min for homogenisation and liposome formation. After homogenisation, the bulk LCS is transferred to another vessel and allowed to stand for at least 5 minutes. An IPC on particle size is performed on the LCS bulk.

(3) Dilution of LCS Bulk, Final Formulation of Liposome Suspension

A 10% (w/w) solution of sucrose is prepared and sterilized. The sucrose solution is mixed with water and LCS bulk in the adequate proportions to get the final liposome suspension (LS) bulk constituted of 21 mg LCS/ml in 5% sucrose solution. pH, sterility, and particle size are tested as in-process controls.

(4) Filling

Vials are filled with 0.4 ml of LS (under continuous agitation) and partially closed for freezing and lyophilisation.

(5) Lyophilisation, Packaging, and Labelling

Vials are frozen at −80° C.±5° C. until lyophilisation proceeds. The lyophilisation process is performed in the range of −45° C. to 25° C. temperature and 0.150 mbars. The process lasts for 24 hours. At the end of lyophilisation vials are fully stoppered in N2 atmosphere, encapsulated, labelled and stored at 5° C.±3° C.

Example 10: Mouse Model

The inventors employed a mouse model of allergy-induced asthma. Also see Tables in the Appendix for individual detailed results in mouse models.

Mice were sensitized to ovalbumin (OVA) by intraperitoneal injection with OVA followed by local exposure to nebulized antigen (i.n.). Sensitized mice were divided into groups—untreated and those treated with the test vaccine or with BCG (positive control)—all administered subcutaneously (s.c.). The inventors also established control groups of the mentioned treatments in non sentitized mice. Increased bronchial reactivity in response to methacholine, as well as the presence of peribronchial eosinophils in those animals exposed to OVA (but not treated), indicated that the allergic process was efficiently induced. BCG vaccination reduced, by almost half, the levels of inflammation (not significant) and bronchial hyper-responsiveness (without reverting to baseline levels). Administration of the FORMULATION A vaccine, an agent according to the present invention, as a preventive measure greatly reduced pulmonary eosinophilia and reversed nearly to baseline bronchial hyperreactivity levels. Use of the FORMULATION A vaccine as a therapeutic agent significantly decreased bronchovascular inflammation, while a tendency towards decreased bronchial hyperresponsiveness in response to the OVA antigen was observed. Based on these results, the inventors conclude that when the FORMULATION A vaccine is administered before the challenge phase, such as 3 times before the challenge phase, it has a clearly beneficial effect on the airways of OVA-challenged mice, while its therapeutic administration clearly reduces inflammation and has a mild effect on bronchial hyperresponsiveness.

Monitoring of individual mice (mucous membranes, hair, and behaviour) did not reveal any adverse effects attributable to the FORMULATION A vaccine, except for a granuloma that appeared at the injection site within days of vaccination. The general condition of mice was normal and equivalent across all groups, treated and untreated, whether sensitized to OVA or not. FIG. 11 shows a consistent and near-uniform increase in the average weight of mice from the 7 groups throughout the experimental period. (See individual data and means±SEM of relevant weights in the Appendix Section).

Unexpectedly, one mouse from the non-sensitized control group under the placebo regimen (Group 1) was found dead in the cage on day −21. The autopsy performed at the Department of Pathology revealed moderate to severe autolysis depending on the area, dense and purulent subcutaneous ventro/inguinal exudate and splenomegaly, which suggested death resulting from a bite or wound infection in the ventro/inguinal zone. The inventors proceeded to replace the mouse by another from the same strain and origin that was a week older and which had not been given any drugs or been subjected to any previous manipulation(s).

Example 11: Effects of Treatments on the Airways

The recruitment of inflammatory cells in the tracheobronchial tree was measured by performing total inflammatory cell and differential cell counts. Also see Tables in the Appendix for individual detailed results in mouse models Differential Counts of BAL Cells To measure overall inflammation, the total number of cells that had accumulated in the BAL was measured and the differential count of inflammatory cells (300 cells stained with Diff-Quick in a cytospin) was performed at a later time. The combined data is presented in FIG. 15, which shows in cells/ml the numbers of eosinophils, macrophages, lymphocytes and neutrophils present per ml of BAL. As indicated in FIG. 15, intense eosinophilia was observed in those animals exposed to OVA, which is a hallmark of inflammatory processes of allergic origin. Eosinophilia was 43.58% lower in the group of animals receiving the BCG vaccine, although this did not attain statistical significance (p=0.08). In parallel to its impact on bronchial reactivity, the FOR- MULATION A vaccine clearly helped curb the degree of eosinophilia, effecting a 61.19% decrease with the therapeutic regimen (T) and 75.81% with the preventive regimen (P) (both p<0005 student's t test). In addition to clearly alleviating eosinophilia, the FORMULATION A vaccine also helped mitigate the increase in lymphocytes, although this only reached statistical significance in the case of T ($p<0.05$ student's t test), remaining constant in the case of P ($p=0.09$ student's t test).

CONCLUSIONS

Based on the results of this project (see examples) one can conclude that administration of the agent described herein, such as FORMULATION A, significantly attenuates airway hyperresponsiveness, eosinophilia and lymphocytosis in the airways of mice exposed to OVA. Under the experimental conditions used its effectiveness exceeds on all the evaluated parameters Pfizer's commercial vaccine BCG Danish 1331 Strain. The therapeutic regimen reduces pulmonary eosinophilia and appears to diminish hyper-reactivity (although not significantly). Compared to Pfizer's commercial vaccine BCG Danish 1331 Strain, the Formulation A vaccine was superior in terms of attenuating pulmonary eosinophilia.

APPENDIX

Data for all Measured Variables

TABLE 6

| Respective weight (g) of each mouse | | | | | | | | | | |
|---|---|---|---|---|---|---|---|---|---|---|
| ID | −31 | −21 | −14 | −7 | 0 | 7 | 14 | 21 | 28 | 31 |
| 1 | 18.72 | 18.88 | 19.12 | 19.06 | 20.17 | 19.96 | 20.62 | 21.42 | 21.42 | 21.79 |
| 2 | 19.44 | 18.57 | 19.5 | 20.7 | 21.27 | 21.9 | 21.25 | 22.83 | 22.07 | 23.02 |
| 3 | 18.41 | 17.19 | 17.98 | 18.57 | 18.99 | 20.16 | 19.6 | 20.06 | 19.81 | 20.85 |
| 4 | 18.45 | 19.24 | 19.39 | 20.36 | 21.36 | 21.28 | 21.54 | 22.69 | 21.77 | 23.19 |
| 5 | 19.47 | 19.04 | 20.3 | 20.74 | 20.4 | 20.61 | 21.1 | 21.96 | 22.25 | 22.43 |
| 6 | 19.24 | 19.65 | 19.2 | 20.8 | 20.82 | 21.12 | 20.73 | 21.18 | 20.8 | 21.61 |
| 7 | 19.09 | 20 | 19.57 | 20.38 | 20.99 | 21.17 | 21.28 | 22.14 | 22.3 | 22.66 |
| 8 | | | 22.63 | 22.48 | 23.39 | 23.34 | 25.35 | 24.47 | 24.61 | 24.99 |
| Mean | 18.97 | 18.94 | 19.71 | 20.39 | 20.92 | 21.19 | 21.43 | 22.09 | 21.88 | 22.57 |
| SEM | 0.169 | 0.343 | 0.475 | 0.419 | 0.443 | 0.379 | 0.598 | 0.463 | 0.491 | 0.442 |
| ID | −31 | −21 | −14 | −7 | 0 | 7 | 14 | 21 | 28 | 31 |
| 9 | 18.93 | 18.77 | 18.74 | 19.04 | 20.67 | 20.71 | 20.42 | 21.68 | 21.58 | 22.15 |
| 10 | 19.6 | 18.88 | 19.1 | 19.73 | 20.99 | 21.42 | 21.77 | 21.18 | 21.18 | 22.69 |
| 11 | 20.02 | 19.73 | 20.04 | 20.9 | 21.02 | 21.12 | 21.41 | 22 | 22.31 | 23.36 |
| 12 | 18.96 | 18.87 | 20.02 | 20.46 | 21.39 | 21.56 | 22.11 | 21 | 21.25 | 22.15 |
| 13 | 17.77 | 18.06 | 18.77 | 19.6 | 20.02 | 20.49 | 20.83 | 20.96 | 20.52 | 20.99 |
| 14 | 17.72 | 19.17 | 18.96 | 19.66 | 19.63 | 19.95 | 20.11 | 20.37 | 20.19 | 22.47 |
| 15 | 17.53 | 18.13 | 18.27 | 18.36 | 19.54 | 19.68 | 19.74 | 20.31 | 20.33 | 21.29 |
| 16 | 18.92 | 19.01 | 19.72 | 19.96 | 20.54 | 21.05 | 22.5 | 22.29 | 22.11 | 23.27 |
| Mean | 18.68 | 18.83 | 19.2 | 19.71 | 20.48 | 20.75 | 21.11 | 21.22 | 21.18 | 22.3 |
| SEM | 0.325 | 0.191 | 0.231 | 0.278 | 0.24 | 0.239 | 0.351 | 0.255 | 0.282 | 0.3 |
| ID | −31 | −21 | −14 | −7 | 0 | 7 | 14 | 21 | 28 | 31 |
| 17 | 18.33 | 18.73 | 18.56 | 18.99 | 19.61 | 19.9 | 20.75 | 21.14 | 21.22 | 21.6 |
| 18 | 19.61 | 19.47 | 19.85 | 20.49 | 21.13 | 21.62 | 22.02 | 21.72 | 21.52 | 22.54 |
| 19 | 19.16 | 19.34 | 19.71 | 20.8 | 21.8 | 22.08 | 22.48 | 22.11 | 22.28 | 23.8 |
| 20 | 18.95 | 19.53 | 19.97 | 21.1 | 21.68 | 22.28 | 22.44 | 21.69 | 22.17 | 23.62 |
| 21 | 18.31 | 17.13 | 18.9 | 20.4 | 20.3 | 20.42 | 20.68 | 20.66 | 20.89 | 21.78 |
| 22 | 19.37 | 19.83 | 19.95 | 21.2 | 21.27 | 20.71 | 21.4 | 21.56 | 21.83 | 23.26 |
| 23 | 19.83 | 19.3 | 19.5 | 19.24 | 20.01 | 19.89 | 20.39 | 20.01 | 21.3 | 21.36 |
| 24 | 17.55 | 16.8 | 17.01 | 17.45 | 19.2 | 19.59 | 19.3 | 19.28 | 19.27 | 19.9 |
| Mean | 18.89 | 18.77 | 19.18 | 19.96 | 20.63 | 20.81 | 21.18 | 21.02 | 21.31 | 22.23 |
| SEM | 0.272 | 0.409 | 0.359 | 0.459 | 0.346 | 0.372 | 0.392 | 0.344 | 0.337 | 0.469 |
| ID | −31 | −21 | −14 | −7 | 0 | 7 | 14 | 21 | 28 | 31 |
| 25 | 18.71 | 18.88 | 19.4 | 19.57 | 20.69 | 20.22 | 21.16 | 21.09 | 21.66 | 22.38 |
| 26 | 18.3 | 18.9 | 19.28 | 19.71 | 20.34 | 20.86 | 21.7 | 21.75 | 21.17 | 23.35 |
| 27 | 21.27 | 20.79 | 20.34 | 20.62 | 21.6 | 22.12 | 22.22 | 22.68 | 22.6 | 23.86 |
| 28 | 20.91 | 20.38 | 20.43 | 21.3 | 21.71 | 22.25 | 22.74 | 21.58 | 22.6 | 23.83 |
| 29 | 18.02 | 17.68 | 18.1 | 19.2 | 19.34 | 20 | 20.13 | 20.35 | 20.18 | 20.79 |
| 30 | 17.85 | 18.25 | 18.5 | 19.9 | 19.81 | 20.36 | 20.95 | 20.65 | 20.87 | 21.37 |
| 31 | 19.42 | 19.8 | 19.81 | 20.3 | 21.58 | 21.29 | 20.95 | 21.62 | 21.64 | 22.53 |
| 32 | 18.16 | 18.53 | 18.72 | 19.39 | 19.87 | 20.59 | 20.35 | 20.48 | 21.96 | 21.98 |
| Mean | 19.08 | 19.15 | 19.32 | 20 | 20.62 | 20.96 | 21.28 | 21.28 | 21.59 | 22.51 |
| SEM | 0.472 | 0.381 | 0.3 | 0.248 | 0.328 | 0.302 | 0.317 | 0.278 | 0.295 | 0.397 |
| ID | −31 | −21 | −14 | −7 | 0 | 7 | 14 | 21 | 28 | 31 |
| 33 | 18.42 | 18.64 | 10.34 | 19.63 | 20.68 | 20.68 | 20.22 | 20.16 | 20.63 | 21.7 |
| 34 | 20.14 | 20.35 | 20.68 | 21.51 | 22.17 | 22.11 | 22.06 | 23.1 | 22.34 | 23.65 |
| 35 | 20.65 | 20.76 | 21.04 | 21.9 | 22.2 | 22.9 | 22.4 | 22.5 | 23.03 | 23.99 |
| 36 | 19.37 | 19.73 | 20.03 | 20.03 | 21.38 | 21.42 | 22.14 | 22.43 | 22.44 | 23.38 |
| 37 | 19.04 | 18.91 | 19.28 | 20.6 | 20.54 | 21.02 | 20.8 | 21.67 | 21.72 | 22.76 |

TABLE 6-continued

| Respective weight (g) of each mouse | | | | | | | | | | |
|---|---|---|---|---|---|---|---|---|---|---|
| 38 | 19.23 | 19.99 | 20.43 | 21.17 | 20.71 | 21.48 | 21.16 | 21.6 | 21.43 | 23.81 |
| 39 | 18 | 19 | 19.55 | 19.59 | 20.45 | 20.5 | 20.15 | 20.76 | 20.9 | 22.35 |
| 40 | 18.64 | 19.08 | 18.85 | 19.27 | 21.3 | 20.9 | 22.1 | 22.6 | 22.68 | 22.58 |
| Mean | 19.19 | 19.56 | 19.9 | 20.46 | 21.18 | 21.38 | 21.38 | 21.85 | 21.9 | 23.03 |
| SEM | 0.311 | 0.27 | 0.272 | 0.347 | 0.25 | 0.283 | 0.323 | 0.354 | 0.306 | 0.285 |
| ID | −31 | −21 | −14 | −7 | 0 | 7 | 14 | 21 | 28 | 31 |
| 41 | 18.71 | 18.54 | 18.75 | 18.88 | 19.38 | 19.51 | 20.01 | 20.56 | 21.19 | 22.03 |
| 42 | 18.8 | 19.47 | 19.85 | 20.49 | 21.03 | 21.45 | 21.25 | 21.94 | 21.65 | 22.94 |
| 43 | 18.88 | 18.79 | 19.58 | 20.5 | 21.24 | 21.25 | 21.84 | 21.81 | 22.84 | 23.93 |
| 44 | 17.8 | 17.88 | 18.95 | 18.99 | 19.73 | 21.4 | 21.39 | 20.79 | 21.3 | 21.11 |
| 45 | 19.18 | 19.98 | 20.16 | 20.18 | 20.31 | 20.95 | 21.12 | 21.31 | 22.05 | 22.48 |
| 46 | 18.12 | 18.71 | 18.53 | 19.46 | 19.85 | 20.46 | 20.72 | 20.96 | 20.8 | 23 |
| 47 | 19.06 | 18.76 | 19.84 | 22.25 | 21.87 | 21.28 | 21.71 | 22.66 | 22.36 | 22.99 |
| 48 | 19.03 | 19.38 | 19.25 | 20.1 | 20.79 | 21.21 | 22.08 | 21.52 | 22.02 | 24 |
| Mean | 18.7 | 18.94 | 19.36 | 20.11 | 20.53 | 20.94 | 21.27 | 21.44 | 21.78 | 22.81 |
| SEM | 0.172 | 0.229 | 0.207 | 0.38 | 0.302 | 0.233 | 0.235 | 0.244 | 0.237 | 0.337 |
| ID | −31 | −21 | −14 | −7 | 0 | 7 | 14 | 21 | 28 | 31 |
| 49 | 19.26 | 18.78 | 19.55 | 19.59 | 20.1 | 21 | 20.8 | 21.02 | 21.04 | 21.73 |
| 50 | 18.61 | 18.95 | 18.8 | 19.41 | 20.4 | 20.3 | 20.58 | 21.62 | 21.73 | 22.69 |
| 51 | 19.53 | 18.75 | 19.05 | 19.38 | 19.65 | 21.39 | 20.66 | 21.08 | 20.91 | 22.48 |
| 52 | 19.28 | 19.66 | 19.82 | 19.45 | 20.09 | 19.83 | 19.8 | 22.09 | 20.38 | 20.85 |
| 53 | 19.14 | 19.15 | 19.33 | 20.16 | 21.02 | 20.9 | 21.95 | 20.09 | 21.95 | 22.03 |
| 54 | 18.72 | 19.36 | 19.55 | 20.17 | 21.86 | 22.39 | 22.4 | 22.22 | 22.12 | 23.16 |
| 55 | 19.4 | 19.88 | 20.14 | 20.8 | 21.6 | 21.48 | 21.58 | 21.5 | 21.97 | 23.39 |
| 56 | 18.82 | 17.98 | 17.95 | 18.26 | 19.13 | 19.65 | 20.51 | 19.8 | 20.2 | 21.7 |
| Mean | 19.1 | 19.06 | 19.27 | 19.65 | 20.48 | 20.87 | 21.04 | 21.18 | 21.29 | 22.25 |
| SEM | 0.119 | 0.211 | 0.24 | 0.266 | 0.335 | 0.324 | 0.305 | 0.309 | 0.267 | 0.298 |

TABLE 7

RL response curve measurements (%) following administration of methacholine, with 100% indicating the baseline level response of each animal RI (%)

| NS vehicle | PBS | 0.625 | 1.25 | 2.5 | 5.00 | 10.00 | 20.00 |
|---|---|---|---|---|---|---|---|
| 1 | 118.43 | 131.34 | 132.35 | 130.24 | 131.20 | 128.26 | 135.64 |
| 2 | 131.56 | 143.87 | 164.19 | 159.04 | 163.17 | 163.12 | 171.09 |
| 3 | 115.04 | 124.55 | 140.42 | 149.96 | 150.90 | 154.81 | 157.01 |
| 4 | 126.74 | 158.81 | 205.26 | 202.11 | 236.54 | 230.00 | 240.59 |
| 5 | 141.56 | 166.45 | 176.68 | 189.07 | 177.78 | 180.28 | 186.48 |
| 6 | 110.66 | 145.91 | 171.89 | 167.32 | 158.36 | 160.71 | 159.57 |
| 7 | 110.37 | 110.55 | 110.73 | 109.07 | 111.01 | 113.30 | 119.83 |
| 8 | 135.97 | 152.16 | 143.86 | 147.44 | 151.21 | 145.80 | 136.84 |
| Mean | 123.79 | 141.71 | 155.67 | 156.78 | 160.02 | 159.53 | 163.38 |
| SEM | 4.21 | 6.56 | 10.50 | 10.63 | 13.08 | 12.49 | 13.35 |
| OVA veh | PBS | 0.625 | 1.25 | 2.5 | 5.00 | 10.00 | 20.00 |
| 9 | 106.86 | 146.71 | 171.29 | 162.44 | 181.44 | 194.87 | 254.44 |
| 10 | 119.43 | 125.96 | 193.79 | 197.44 | 199.27 | 224.99 | 233.58 |
| 11 | 122.53 | 241.41 | 252.50 | 314.73 | 353.16 | 328.97 | 347.92 |
| 12 | 129.22 | 304.31 | 340.14 | 289.46 | 345.92 | 445.23 | 597.87 |
| 13 | 130.91 | 193.30 | 223.68 | 254.45 | 258.39 | 272.47 | 275.50 |
| 14 | 135.49 | 151.47 | 166.99 | 392.55 | 478.27 | 480.22 | 409.83 |
| 15 | 124.92 | 142.11 | 215.72 | 199.42 | 294.69 | 248.12 | 319.51 |
| 16 | 126.79 | 129.46 | 138.57 | 149.23 | 166.47 | 177.93 | 223.34 |
| Mean | 124.52 | 179.34 | 212.84 | 244.97 | 284.70 | 296.60 | 332.75 |
| SEM | 3.08 | 22.45 | 22.20 | 29.59 | 37.47 | 39.94 | 43.88 |
| NS BCG | PBS | 0.625 | 1.25 | 2.5 | 5.00 | 10.00 | 20.00 |
| 17 | 146.66 | 162.48 | 154.77 | 160.04 | 161.29 | 161.04 | 147.63 |
| 18 | 136.70 | 165.00 | 160.13 | 145.98 | 152.23 | 164.46 | 161.56 |
| 19 | 130.02 | 155.93 | 167.91 | 191.58 | 203.82 | 186.27 | 246.22 |
| 20 | 153.91 | 182.18 | 203.31 | 240.48 | 238.37 | 234.70 | 224.65 |
| 21 | 133.25 | 137.28 | 162.11 | 178.48 | 191.91 | 199.33 | 205.70 |
| 22 | 136.78 | 149.59 | 195.96 | 282.79 | 292.65 | 292.72 | 301.94 |
| 23 | 118.33 | 131.98 | 137.02 | 142.47 | 145.38 | 148.28 | 155.10 |

TABLE 7-continued

| RL response curve measurements (%) following administration of methacholine, with 100% indicating the baseline level response of each animal RI (%) | | | | | | | |
|---|---|---|---|---|---|---|---|
| 24 | 126.74 | 137.82 | 162.24 | 204.57 | 207.56 | 229.82 | 283.77 |
| Mean | 135.30 | 152.78 | 167.93 | 193.30 | 199.15 | 202.08 | 215.82 |
| SEM | 3.95 | 6.01 | 7.67 | 17.17 | 17.40 | 17.06 | 20.88 |
| OVA BCG | PBS | 0.625 | 1.25 | 2.5 | 5.00 | 10.00 | 20.00 |
| 25 | 108.03 | 138.21 | 183.32 | 202.26 | 202.73 | 182.79 | 185.49 |
| 26 | 118.25 | 257.81 | 206.97 | 216.36 | 212.99 | 204.10 | 206.23 |
| 27 | 134.80 | 222.02 | 236.12 | 280.32 | 280.29 | 283.06 | 282.43 |
| 28 | 115.15 | 114.03 | 118.00 | 120.39 | 121.71 | 142.98 | 186.51 |
| 29 | 115.43 | 129.98 | 150.67 | 180.26 | 171.38 | 174.01 | 185.08 |
| 30 | 126.05 | 125.12 | 129.19 | 151.90 | 275.44 | 344.08 | 364.32 |
| 31 | 129.02 | 136.77 | 267.38 | 261.84 | 330.42 | 461.90 | 371.06 |
| 32 | 109.68 | 128.89 | 146.11 | 149.87 | 168.38 | 173.64 | 217.46 |
| Mean | 119.55 | 156.60 | 179.72 | 195.40 | 220.42 | 245.82 | 249.82 |
| SEM | 3.36 | 18.68 | 18.88 | 19.79 | 24.62 | 38.82 | 28.08 |
| NS FORMULATION A P | PBS | 0.625 | 1.25 | 2.5 | 5.00 | 10.00 | 20.00 |
| 33 | 125.58 | 144.20 | 168.15 | 186.86 | 175.24 | 176.33 | 177.47 |
| 34 | 146.51 | 169.00 | 260.52 | 250.91 | 252.07 | 246.81 | 249.22 |
| 35 | 140.23 | 142.84 | 148.36 | 161.59 | 199.77 | 204.06 | 212.82 |
| 36 | 126.99 | 155.93 | 160.95 | 177.39 | 186.67 | 176.74 | 196.50 |
| NS FORMULATION A P | PB | 0.625 | 1.25 | 2.5 | 5.00 | 10.00 | 20.00 |
| 33 | 125.58 | 144.20 | 168.15 | 186.86 | 175.24 | 176.33 | 177.47 |
| 34 | 146.51 | 169.00 | 260.52 | 250.91 | 252.07 | 246.81 | 249.22 |
| 35 | 140.23 | 142.84 | 148.36 | 161.59 | 199.77 | 204.06 | 212.82 |
| 36 | 126.99 | 155.93 | 160.95 | 177.39 | 186.67 | 176.74 | 196.50 |
| OVA FORMULATION A P | PBS | 0.625 | 1.25 | 2.5 | 5.00 | 10.00 | 20.00 |
| 41 | 105.56 | 127.62 | 153.09 | 152.64 | 155.79 | 155.05 | 141.78 |
| 42 | 127.83 | 146.48 | 149.40 | 150.02 | 157.59 | 158.28 | 167.28 |
| 43 | 132.88 | 171.37 | 178.22 | 185.08 | 192.45 | 276.23 | 295.46 |
| 44 | 106.69 | 156.07 | 185.86 | 200.16 | 190.12 | 206.75 | 217.86 |
| 45 | 112.65 | 146.94 | 195.29 | 209.32 | 233.57 | 222.81 | 239.62 |
| 46 | 131.19 | 157.88 | 183.77 | 191.72 | 195.83 | 204.58 | 218.59 |
| 47 | 103.71 | 118.27 | 129.55 | 137.52 | 146.41 | 151.73 | 159.29 |
| 48 | 143.41 | 152.30 | 154.25 | 178.90 | 188.66 | 188.85 | 221.45 |
| Mean | 120.49 | 147.12 | 166.18 | 175.67 | 182.55 | 195.53 | 207.67 |
| SEM | 5.35 | 6.01 | 8.05 | 9.19 | 10.02 | 14.91 | 17.65 |
| OVA FORMULATION A T | PBS | 0.625 | 1.25 | 2.5 | 5.00 | 10.00 | 20.00 |
| 49 | 132.93 | 162.46 | 160.75 | 163.44 | 159.13 | 160.92 | 156.80 |
| 50 | 186.62 | 219.08 | 214.06 | 233.51 | 222.61 | 221.68 | 212.96 |
| 51 | 138.92 | 205.77 | 243.49 | 261.02 | 266.60 | 276.19 | 280.05 |
| 52 | 125.73 | 155.11 | 170.70 | 189.33 | 211.72 | 321.32 | 271.59 |
| 53 | 111.64 | 147.12 | 208.05 | 235.99 | 249.64 | 280.12 | 274.40 |
| 54 | 131.74 | 213.92 | 241.73 | 236.14 | 240.46 | 214.20 | 216.79 |
| 55 | 110.04 | 108.98 | 133.52 | 145.54 | 142.20 | 151.71 | 178.89 |
| 56 | 142.13 | 315.65 | 405.81 | 421.56 | 438.06 | 518.91 | 459.26 |
| Mean | 134.97 | 191.01 | 222.26 | 235.82 | 241.30 | 268.13 | 256.34 |
| SEM | 8.45 | 22.29 | 29.61 | 30.09 | 31.97 | 41.41 | 33.18 |

TABLE 8

| Individual inflammatory cell counts | | | | | | |
|---|---|---|---|---|---|---|
| NS | OVA | NS BCG | OVA BCG | NS Form A P | OVA Form A P | OVA Form A T |
| 425000 | 520000 | 540000 | 370000 | 260000 | 275000 | 370000 |
| 245000 | 615000 | 355000 | 605000 | 300000 | 450000 | 355000 |

TABLE 8-continued

| Individual inflammatory cell counts | | | | | | | |
|---|---|---|---|---|---|---|---|
| | NS | OVA | NS BCG | OVA BCG | NS Form A P | OVA Form A P | OVA Form A T |
| | 245000 | 440000 | 495000 | 345000 | 335000 | 395000 | 480000 |
| | 295000 | 375000 | 260000 | 240000 | 205000 | 310000 | 210000 |
| | 255000 | 280000 | 165000 | 295000 | 275000 | 315000 | 225000 |
| | 215000 | 330000 | 105000 | 275000 | 260000 | 245000 | 400000 |
| | 255000 | 430000 | 210000 | 205000 | 250000 | 390000 | 275000 |
| | 105000 | 575000 | 315000 | 160000 | 265000 | 255000 | 280000 |
| Mean | 255000 | 445625 | 305625 | 311875 | 268750 | 329375 | 324375 |
| SEM | 31282.13 | 41623.71 | 54210.55 | 48494.64 | 13354.71 | 26295.67 | 32820.36 |

TABLE 9

| Individual differential cell counts (%, BAL) | | | | | | | | |
|---|---|---|---|---|---|---|---|---|
| | NS | | | | OVA | | | |
| | eos | macro | neutro | lymph | eos | macro | neutro | lymph |
| | 0.00 | 95.65 | 3.62 | 0.72 | 20.67 | 61.00 | 10.00 | 8.33 |
| | 0.00 | 92.31 | 2.68 | 5.02 | 14.05 | 62.21 | 6.35 | 17.39 |
| | 2.35 | 77.93 | 11.27 | 8.45 | 51.99 | 27.56 | 9.66 | 10.80 |
| | 0.65 | 87.91 | 3.59 | 7.84 | 54.88 | 30.64 | 6.06 | 8.42 |
| | 0.33 | 80.67 | 11.67 | 7.33 | 17.63 | 54.17 | 14.10 | 14.10 |
| | 0.31 | 92.50 | 1.88 | 5.31 | 57.00 | 19.67 | 2.67 | 20.67 |
| | 4.73 | 71.62 | 14.53 | 9.12 | 43.52 | 24.58 | 8.97 | 22.92 |
| | 3.54 | 80.30 | 9.60 | 6.57 | 52.00 | 22.00 | 6.00 | 20.00 |
| Mean | 1.49 | 84.86 | 7.35 | 6.30 | 38.97 | 37.73 | 7.98 | 15.33 |
| SEM | 0.64 | 2.99 | 1.74 | 0.94 | 6.48 | 6.42 | 1.22 | 2.03 |
| | NS BCG | | | | OVA BCG | | | |
| | eos | macro | neutro | lymph | eos | macro | neutro | lymph |
| | 0.32 | 91.75 | 2.54 | 5.40 | 18.33 | 65.33 | 3.00 | 13.33 |
| | 0.00 | 94.83 | 1.72 | 3.45 | 40.86 | 33.89 | 8.97 | 16.28 |
| | 0.99 | 92.11 | 5.26 | 1.64 | 48.85 | 30.82 | 8.52 | 11.80 |
| | 3.40 | 84.35 | 8.84 | 3.40 | 18.24 | 53.82 | 13.24 | 14.71 |
| | 0.66 | 88.82 | 5.26 | 5.26 | 25.81 | 55.81 | 8.39 | 10.00 |
| | 2.33 | 63.67 | 12.33 | 21.6 | 14.20 | 67.19 | 4.42 | 14.20 |
| | 4.00 | 71.00 | 12.67 | 12.33 | 38.55 | 27.41 | 6.93 | 27.11 |
| | 4.04 | 64.31 | 6.40 | 25.25 | 25.82 | 72.13 | 0.41 | 1.64 |
| Mean | 1.97 | 81.35 | 6.88 | 9.80 | 28.83 | 50.80 | 6.73 | 13.63 |
| SEM | 0.60 | 4.59 | 1.45 | 3.20 | 4.42 | 6.27 | 1.42 | 2.50 |

| | NS RUTI P | | | | OVA Form. A P | | | | OVA Form. A T | | | |
|---|---|---|---|---|---|---|---|---|---|---|---|---|
| | eos | macro | neutro | linfo | eos | macro | neutro | linfo | eos | macro | neutro | linfo |
| | 1.59 | 72.73 | 9.77 | 15.91 | 2.86 | 85.71 | 3.49 | 7.94 | 18.06 | 60.54 | 7.69 | 13.71 |
| | 0.29 | 85.00 | 9.12 | 5.59 | 0.48 | 83.73 | 8.13 | 7.66 | 7.80 | 74.24 | 10.17 | 7.80 |
| | 1.02 | 75.09 | 9.90 | 13.99 | 23.91 | 49.69 | 11.49 | 14.91 | 6.25 | 83.04 | 3.57 | 7.14 |
| | 0.00 | 88.22 | 7.74 | 4.04 | 35.18 | 43.97 | 6.51 | 14.33 | 38.74 | 31.79 | 17.55 | 11.92 |
| | 0.34 | 60.20 | 30.95 | 8.50 | 6.21 | 81.05 | 2.29 | 10.46 | 43.67 | 36.67 | 5.00 | 14.67 |
| | 0.67 | 82.67 | 4.00 | 12.67 | 2.97 | 69.80 | 9.90 | 17.33 | 20.38 | 57.96 | 8.92 | 12.74 |
| | 0.00 | 86.89 | 3.28 | 9.84 | 0.00 | 80.55 | 3.41 | 16.04 | 14.05 | 62.21 | 6.35 | 17.39 |
| | 0.00 | 72.67 | 8.00 | 19.33 | 34.02 | 24.74 | 14.78 | 26.46 | 35.88 | 26.58 | 21.26 | 16.28 |
| Mean | 0.49 | 77.93 | 10.35 | 11.23 | 13.20 | 64.91 | 7.50 | 14.39 | 23.10 | 54.13 | 10.06 | 12.71 |
| SEM | 0.20 | 3.37 | 3.07 | 1.84 | 5.39 | 8.02 | 1.56 | 2.15 | 5.11 | 7.23 | 2.20 | 1.30 |

TABLE 10

| Individual results of the BAL differential cell counts (cells/ml) | | | | | | | | |
|---|---|---|---|---|---|---|---|---|
| | NS | | | | OVA | | | |
| | eos | macro | neutro | lymph | eos | macro | neutro | lymph |
| | 0.00 | 406521.74 | 15398.55 | 3079.71 | 107466.67 | 317200.00 | 52000.00 | 43333.33 |
| | 0.00 | 226153.85 | 6555.18 | 12290.97 | 86387.96 | 382575.75 | 39080.77 | 106956.52 |

TABLE 10-continued

Individual results of the BAL differential cell counts (cells/ml)

| | | | | | | | | |
|---|---|---|---|---|---|---|---|---|
| | 5751.17 | 190938.97 | 27605.63 | 20704.23 | 228750.00 | 121250.00 | 42500.00 | 47500.00 |
| | 1928.10 | 259330.07 | 10604.58 | 23137.25 | 205808.08 | 114898.99 | 22727.27 | 31565.66 |
| | 850.00 | 205700.00 | 29750.00 | 18700.00 | 49358.97 | 151666.67 | 39487.18 | 39487.18 |
| | 671.88 | 198875.00 | 4031.25 | 11421.88 | 188100.00 | 64900.00 | 8800.00 | 68200.00 |
| | 12060.81 | 182635.14 | 37043.92 | 23260.14 | 187142.86 | 105714.29 | 38571.43 | 98571.43 |
| | 3712.12 | 84318.18 | 10075.76 | 6893.94 | 299000.00 | 126500.00 | 34500.00 | 115000.00 |
| Mean | 3121.76 | 219309.12 | 17633.11 | 14936.01 | 169001.82 | 173088.15 | 34708.27 | 68826.76 |
| SEM | 1459.25 | 32091.46 | 4314.20 | 2701.14 | 29106.93 | 39999.89 | 4689.31 | 11820.78 |

| | NS BCG | | | | OVA BCG | | | |
|---|---|---|---|---|---|---|---|---|
| | eos | macro | neutro | lymph | eos | macro | neutro | lymph |
| | 1714.29 | 495428.57 | 13714.29 | 29142.86 | 67833.33 | 241733.33 | 11100.00 | 49333.33 |
| | 0.00 | 336637.93 | 6120.69 | 12241.38 | 247225.91 | 205016.61 | 54269.10 | 98488.37 |
| | 4884.87 | 455921.05 | 26052.63 | 8141.45 | 168540.98 | 106327.87 | 29409.84 | 40721.31 |
| | 8843.54 | 219319.73 | 22993.20 | 8843.54 | 43764.71 | 129176.47 | 31764.71 | 35294.12 |
| | 1085.53 | 146546.05 | 8684.21 | 8684.21 | 76129.03 | 164629.03 | 24741.94 | 29500.00 |
| | 2450.00 | 66850.00 | 12950.00 | 22750.00 | 39037.85 | 184779.18 | 12145.11 | 39037.85 |
| | 8400.00 | 149100.00 | 26600.00 | 25900.00 | 79036.14 | 56189.76 | 14201.81 | 55572.29 |
| | 12727.27 | 202575.73 | 20151.52 | 79545.45 | 41311.48 | 115409.84 | 655.74 | 2622.95 |
| Mean | 5013.19 | 259047.39 | 17158.32 | 24406.11 | 95359.93 | 150407.76 | 22286.03 | 43821.28 |
| SEM | 1601.77 | 54626.61 | 2785.39 | 8419.42 | 26243.44 | 21213.97 | 5871.74 | 9603.35 |

| NS Form. A P | | | OVA Form. A P | | | | OVA Form. A T | | | |
|---|---|---|---|---|---|---|---|---|---|---|
| macro | neutro | linfo | eos | macro | neutro | linfo | eos | macro | neutro | linfo |
| 89090.91 | 25409.09 | 41363.64 | 7857.14 | 235714.29 | 9603.17 | 21825.40 | 66822.74 | 223979.93 | 28461.54 | 50735.79 |
| 55000.00 | 27352.94 | 16764.71 | 2153.11 | 376794.26 | 36602.87 | 34449.76 | 27677.97 | 263542.37 | 36101.69 | 27677.97 |
| 51535.84 | 33157.00 | 46877.13 | 94456.52 | 196273.29 | 45388.20 | 58881.99 | 30000.00 | 398571.43 | 17142.86 | 34285.71 |
| 80841.75 | 15875.42 | 8282.83 | 109055.37 | 136319.22 | 20195.44 | 44429.97 | 81357.62 | 66754.97 | 36854.30 | 25033.11 |
| 65561.22 | 85119.05 | 23384.35 | 19558.82 | 255294.12 | 7205.88 | 32941.18 | 98250.00 | 82500.00 | 11250.00 | 33000.00 |
| 14933.33 | 10400.00 | 32933.33 | 7277.23 | 171014.85 | 24257.43 | 42450.50 | 81528.66 | 231847.13 | 35668.79 | 50955.41 |
| 17213.11 | 8196.72 | 24590.16 | 0.00 | 314129.69 | 13310.58 | 62559.73 | 38628.76 | 171070.23 | 17474.92 | 47826.09 |
| 92566.67 | 21200.00 | 51233.33 | 86752.58 | 63092.78 | 37680.41 | 67474.23 | 100465.12 | 74418.60 | 59534.88 | 45581.40 |
| 08342.85 | 28338.78 | 30678.69 | 40888.85 | 218579.06 | 24280.50 | 45626.59 | 65591.36 | 189085.58 | 30311.12 | 39386.93 |
| 11472.59 | 8650.53 | 5327.80 | 16619.59 | 35230.40 | 5037.23 | 5675.15 | 10537.35 | 40592.19 | 5451.07 | 3737.27 |

The invention claimed is:

1. A method of treating an allergic response in a subject suffering from an allergic response, the method comprising administering to said subject an agent, wherein the agent is:

(i) a liposome formulation comprising:

(a) fragments from a *Mycobacterium tuberculosis*-complex (MTB-C) strain (FCMtb), wherein said fragments are capable of reducing inflammation associated with said allergic response;

(b) a liposome forming agent; and (c) 1 to 20% sucrose; or (ii) a liposome formulation comprising:

(a) fragments from a *Mycobacterium tuberculosis*-complex (MTB-C) strain (FCMtb), wherein said fragments are capable of reducing inflammation associated with said allergic response; and (b) a liposome forming agent; wherein the liposome formulation comprises liposome particles having a z-average particle size of 150 nm or less, such that said allergic response in said subject suffering from an allergic response is treated.

2. The method according to claim 1, wherein the liposome formulation (i) comprises liposome particles having the z-average particle size of 150 nm or less.

3. The method according to claim 2, wherein the liposome formulation (i) or (ii) comprises liposome particles having a z-average particle size between 40 and 135 nm, or wherein the liposome formulation (i) or (ii) is an emulsion comprising liposome particles having a z-average particle size of below 40 nm.

4. The method according to claim 1, wherein the liposome formulation (i) or (ii) comprises liposome particles having polydispersity index of 0.4 or less.

5. The method according to claim 1, wherein the *Mycobacterium tuberculosis*-complex (MTB-C) strain is a virulent *Mycobacterium tuberculosis*-complex (MTB-C) strain or is the MTB-C strain NCTC 13536, deposited in 2010 at the NCTC in London.

6. The method according to claim 1, wherein the agent additionally comprises (d) a tensioactive agent selected from the group consisting of cholate, deoxycholate, cholesterol and cholesterol hemisuccinate; or one or more non-ionic surfactant selected from the group consisting of alkylphenol ethoxylates and sorbitan ester ethoxylates.

7. The method according to claim 1, wherein the fragments of MTB-C strain comprise cell wall fragments.

8. The method according to claim 1, wherein the liposome forming agent is selected from the group consisting of a hydrogenated, partially hydrogenated and non-hydrogenated phospholipid.

9. The method according to claim 1, wherein the fragments from the *Mycobacterium tuberculosis*-complex (MTB-C) strain (FCMtb) comprise at least two of the following polypeptides:

(i) a first polypeptide having a molecular weight of about 70 kDa as measured following electrophoresis on a sodium dodecylsulfate (SDS) polyacrylamide gel, similar to *M. tuberculosis* HSP70 protein (Rv0350);

(ii) a second polypeptide having a molecular weight of about 38 kDa as measured following electrophoresis on a sodium dodecylsulfate (SDS) polyacrylamide gel, similar to *M. tuberculosis* 38 kDa protein (Rv 0934);

(iii) a third polypeptide having a molecular weight of about 30 kDa as measured following electrophoresis on a sodium dodecylsulfate (SDS) polyacrylamide gel, similar to *M. tuberculosis* Ag85B protein (Rv 1866c);

(iv) a fourth polypeptide having a molecular weight of about 10 kDa as measured following electrophoresis on a sodium dodecylsulfate (SDS) polyacrylamide gel, similar to *M. tuberculosis* CFP10 protein (Rv3874); and (v) a fifth polypeptide having a molecular weight of about 6 kDa as measured following electrophoresis on a sodium dodecylsulfate (SDS) polyacrylamide gel, similar to *M. tuberculosis* ESAT-6 protein (Rv3875).

10. The method according to claim 1, wherein the agent comprises at least one antigen of *Mycobacterium tuberculosis* selected from the group consisting of HSP70, 38 kDa protein and Ag85B, or a fragment thereof.

11. The method according to claim 1, wherein the agent additionally comprises one or more mycolic acids and/or a sugar-conjugated mycolate; or one or more salts or a solution thereof.

12. The method according to claim 1, wherein the liposome formulation is freeze-dried.

13. The method according to claim 1, wherein the agent is administered as a part of a pharmaceutical composition comprising a pharmaceutically acceptable carrier.

14. The method according to claim 1, wherein the allergic response is IgE-mediated.

15. The method according to claim 1, wherein the allergic response is atopy, respiratory dysfunction and/or broncho-vascular inflammation, asthma, hay fever, rhinitis or eczema.

16. The method according to claim 15, wherein the response is asthma.

17. The method according to claim 16, wherein the asthma is bronchial asthma.

18. The method according to claim 1, wherein the agent is administered by injection, by inhalation or sublingually.

19. The method according to claim 1, wherein the agent is administered at the dose of 200 μg or less.

20. The method according to claim 19, wherein the agent is administered at least two times.

21. The method according to claim 1, wherein the agent is administered in intervals of one week or more.

* * * * *